United States Patent
Napier et al.

(10) Patent No.: US 8,013,216 B2
(45) Date of Patent: Sep. 6, 2011

(54) METHOD FOR THE PRODUCTION OF γ-LINOLENIC ACID AND/OR STEARIDONIC ACID IN TRANSGENIC BRASSICACEAE AND LINACEAE

(75) Inventors: Johnathan A. Napier, Preston (GB); Olga Sayanova, St. Albans (GB); Monica Venegas Caleron, Harpenden (GB)

(73) Assignee: BASF Plant Science GmbH, Ludwigshafen (DE)

( * ) Notice: Subject to any disclaimer, the term of this patent is extended or adjusted under 35 U.S.C. 154(b) by 553 days.

(21) Appl. No.: 12/091,779

(22) PCT Filed: Oct. 30, 2006

(86) PCT No.: PCT/EP2006/010408
§ 371 (c)(1),
(2), (4) Date: Apr. 28, 2008

(87) PCT Pub. No.: WO2007/051577
PCT Pub. Date: May 10, 2007

(65) Prior Publication Data
US 2008/0229454 A1   Sep. 18, 2008

(30) Foreign Application Priority Data
Nov. 2, 2005 (DE) .......................... 10 2005 052 551

(51) Int. Cl.
*A01H 5/00* (2006.01)
*C12N 15/82* (2006.01)
*C07H 21/04* (2006.01)

(52) U.S. Cl. ......................... 800/298; 800/281; 536/23.2
(58) Field of Classification Search ........................ None
See application file for complete search history.

(56) References Cited

U.S. PATENT DOCUMENTS
5,614,393 A   3/1997   Thomas et al.

FOREIGN PATENT DOCUMENTS

| | | |
|---|---|---|
| CA | 2180154 | 7/1995 |
| EP | 0550162 A1 | 7/1993 |
| EP | 0794250 A1 | 9/1997 |
| WO | WO-91/13972 A1 | 9/1991 |
| WO | WO-93/06712 A1 | 4/1993 |
| WO | WO-93/11245 A1 | 6/1993 |
| WO | WO-94/11516 A1 | 5/1994 |
| WO | WO-94/18337 A1 | 8/1994 |
| WO | WO-95/18222 A1 | 7/1995 |
| WO | WO-96/21022 A1 | 7/1996 |
| WO | WO-97/21340 A1 | 6/1997 |
| WO | WO-97/30582 A1 | 8/1997 |
| WO | WO-98/46465 A1 | 10/1998 |
| WO | WO-98/46763 A1 | 10/1998 |
| WO | WO-98/46764 A1 | 10/1998 |
| WO | WO-98/46776 A2 | 10/1998 |
| WO | WO-99/27111 A1 | 6/1999 |
| WO | WO-99/64616 A2 | 12/1999 |
| WO | WO-00/21557 A1 | 4/2000 |
| WO | WO-2005/021761 A1 | 3/2005 |
| WO | WO-2005/102310 A1 | 11/2005 |

OTHER PUBLICATIONS

Sequence alignment of SEQ ID No. 2 with Sayanova et al, run date Oct. 5, 2010.*
Poulos, A., "Very Long Chain Fatty Acids in Higher Animals—A Review", Lipids, 1995, vol. 30, No. 1, pp. 1-14.
Horrocks, L. A. et al., "Health Benefits of Docosahexaenoic Acid (DHA)", Pharmacological Research, 1999, vol. 40, No. 3, pp. 211-225.
Stukey, J. E., et al., "The OLE1 Gene of *Saccharomyces cerevisiae* Encodes the Δ9 Fatty Acid Desaturase and Can Be Functionally Replaced by the Rat Stearoyl-CoA Desaturase Gene", The Journal of Biological Chemistry, 1990, vol. 265, No. 33, pp. 20144-20149.
Wada, H., et al., "Enhancement of Chilling Tolerance of a Cyanobacterium by Genetic Manipulation of Fatty Acid Desaturation", Nature, 1990, vol. 347, pp. 200-203.
Huang, Y-S., et al., "Cloning of Δ12- and Δ6-Desaturases from *Mortierella alpina* and Recombinant Production of γ-Linolenic Acid in *Saccharomyces cerevisiae*", Lipids, 1999, vol. 34, No. 7, pp. 649-659.
McKeon, T., et al., "Stearoyl-Acyl Carrier Protein Desaturase from Safflower Seeds", Methods in Enzymology, 1981, vol. 71, Part C, Lipids, pp. 275-277.
Wang, X. M., et al., "Biosynthesis and Regulation of Linolenic Acid in Higher Plants", Plant Physiol. Biochem 1988, vol. 26, No. 6, pp. 777-792.
Sayanova, O., et al., "Identification of *Primula* "Front-End" Desaturases with Distinct n-6 or n-3 Substrate Preferences", Planta, 2006, vol. 224, pp. 1269-1277.
Sayanova, O., et al., "Δ6-Unsaturated Fatty Acids in Species and Tissues of the Primulaceae", Phytochemistry, 1999, vol. 52, pp. 419-422.
Sayanova, O. V., et al., "Identification of *Primula* Fatty Acid Δ6-Desaturases with n-3 Substrate Preferences", FEBS Letters, 2003, vol. 542, pp. 100-104.
Hong, H., et al., "High-Level Production of γ-Linolenic Acid in *Brassica juncea* Using a Δ6 Desaturase from *Pythium irregulare*", Plant Physiology, 2002, vol. 129, pp. 354-362.

* cited by examiner

*Primary Examiner* — Elizabeth McElwain
(74) *Attorney, Agent, or Firm* — Connolly Bove Lodge & Hutz, LLP

(57) ABSTRACT

The present invention relates to the production of γ-linolenic acid ($18:3^{\Delta 6,9,12}$) or stearidonic acid ($18:4^{\Delta 6,9,12,15}$) or γ-linolenic acid ($18:3^{\Delta 6,9,12}$) and stearidonic acid ($18:4^{\Delta 6,9,12,15}$) in transgenic plants of the family Brassicaceae, where the transgenic plants comprise at least 10% by weight of oleic acid based on the total fatty acid content and, as the result of the activity of the Δ6-desaturases used in the method, have an increased Δ6-C18-fatty acid content. The invention furthermore relates to novel nucleic acid sequences which code for the Δ6-desaturases used in the method, gene constructs comprising these nucleic acid sequences, a vector and transgenic plants comprising at least one nucleic acid sequence or a gene construct.

18 Claims, 4 Drawing Sheets

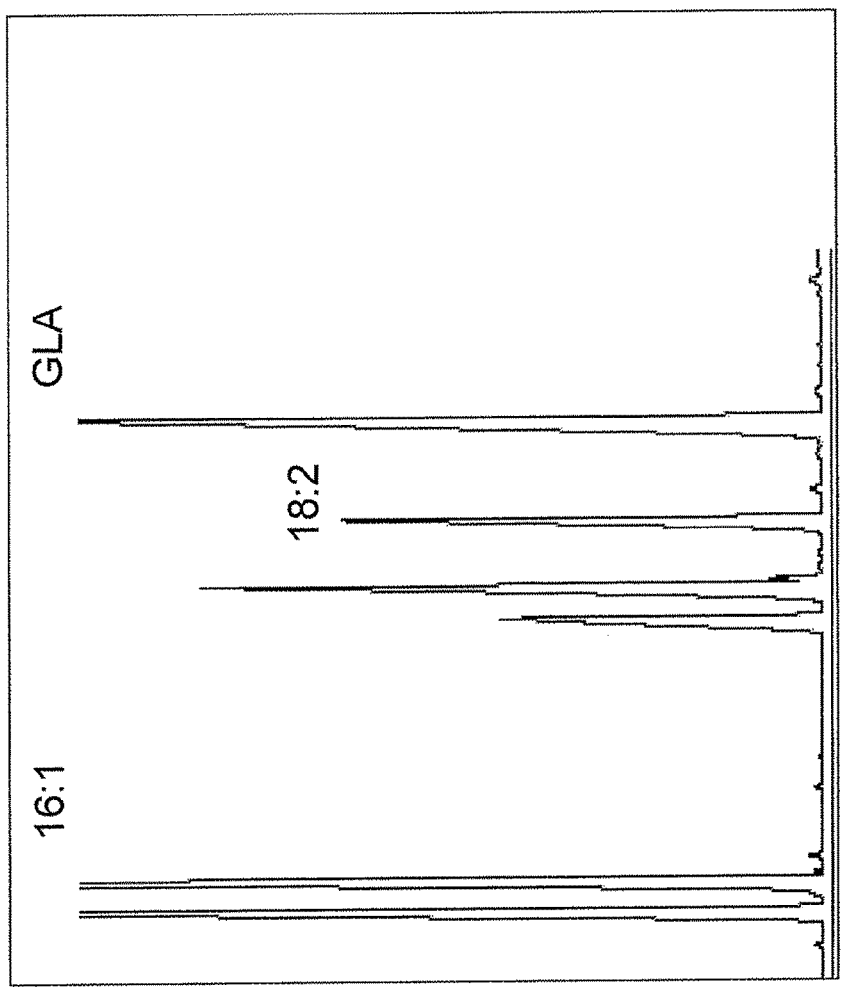
Figure 1: Gas-chromatographic analysis of yeasts which comprise the plasmid pYCort6 and which have been fed 18:2. The newly formed fatty acid is $\gamma 18:3^{\Delta 6, 9, 12}$ ($\gamma$-linolenic acid = GLA).

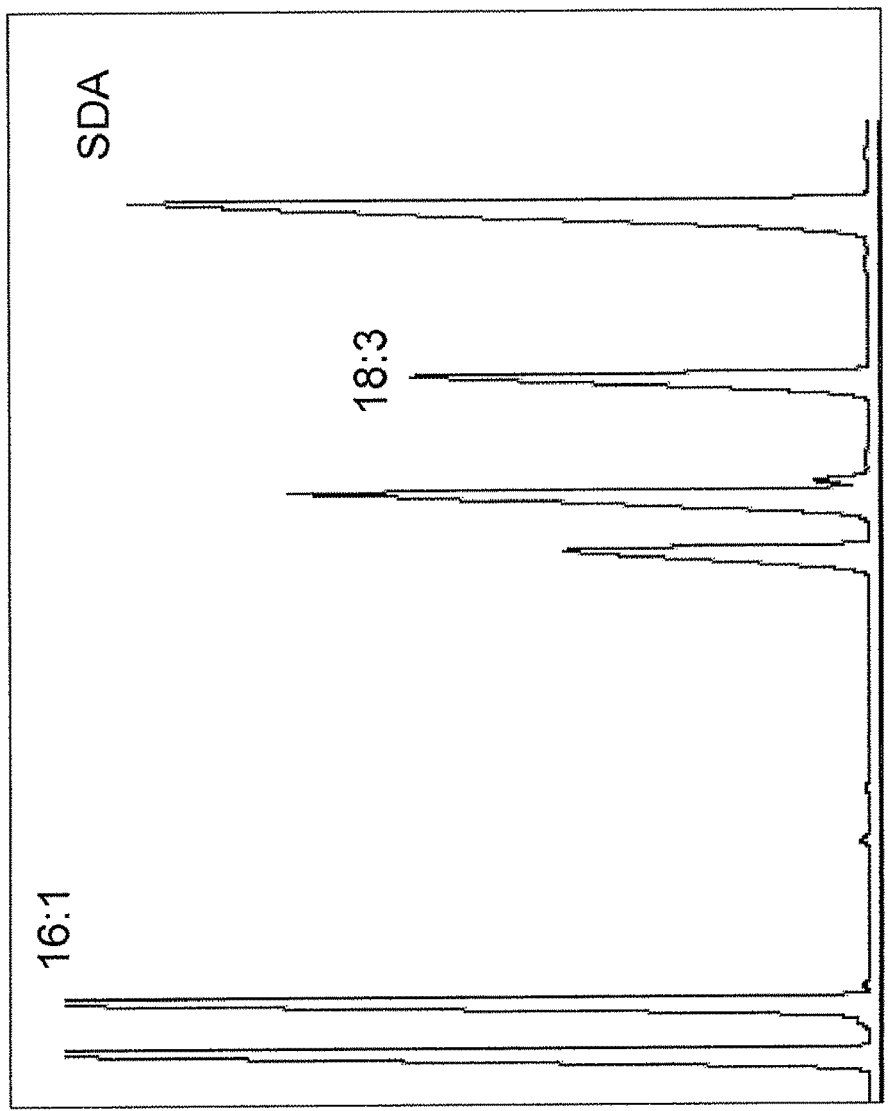
Figure 2: Fatty acid pattern of yeasts had been transformed with the construct pYLut6 and fed the fatty acid 18:3 $\Delta 9, 12, 15$. The corresponding fatty acids are identified. SDA (stearidonic acid) corresponds to 18:4 $\Delta 6, 9, 12, 15$

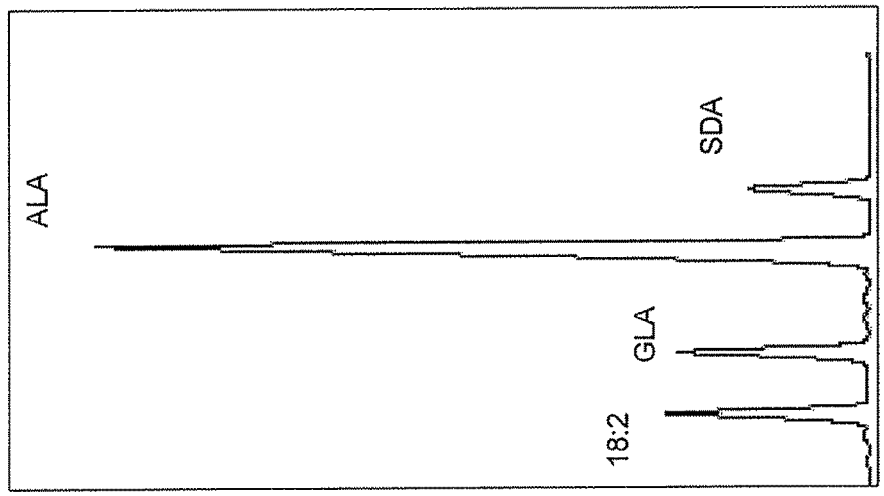
Figure 3: Gas-chromatographic analysis of the fatty acids from leaf material of Arabidopsis plants which had been transformed with the plasmid pBIN-Cort6.

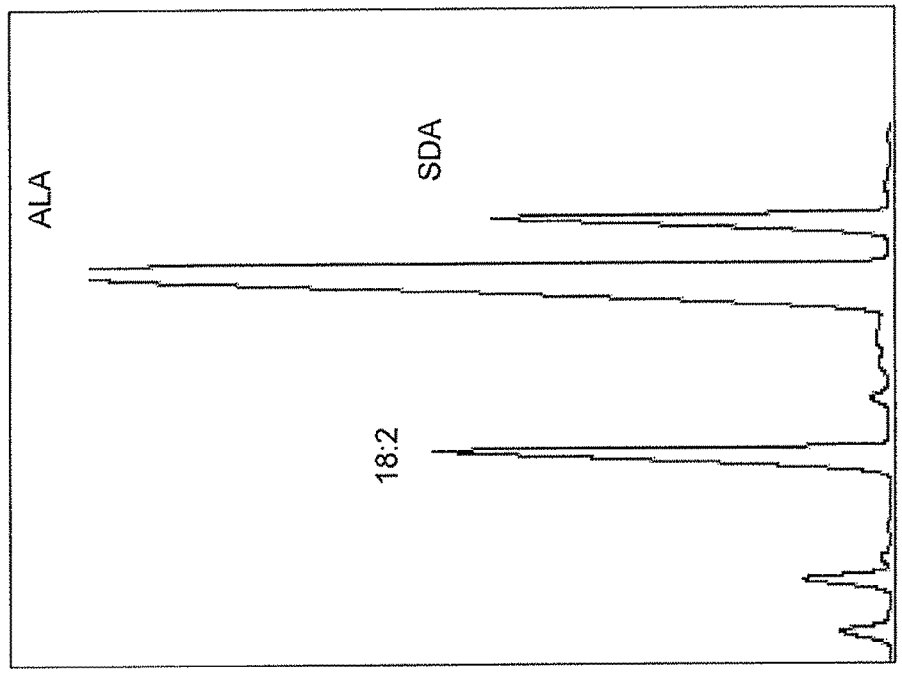
Figure 4: Gas-chromatographic analysis of the fatty acids from leaf material of Arabidopsis plants which had been transformed with the plasmid pBIN-Lut6.

SEQUENCE LISTING

```
<160> NUMBER OF SEQ ID NOS: 14

<210> SEQ ID NO 1
<211> LENGTH: 1350
<212> TYPE: DNA
<213> ORGANISM: Primula lutoides
<220> FEATURE:
<221> NAME/KEY: CDS
<222> LOCATION: (1)..(1350)
<223> OTHER INFORMATION: Delta-6-desaturase

<400> SEQUENCE: 1 atg gct aac aaa tct caa aca ggt tac ata acg agc tca gaa ctg gaa      48
Met Ala Asn Lys Ser Gln Thr Gly Tyr Ile Thr Ser Ser Glu Leu Glu
1               5                   10                  15 acc cac aac aag gca gga gac cta tgg ata tca ata cac ggg cag gtc      96
Thr His Asn Lys Ala Gly Asp Leu Trp Ile Ser Ile His Gly Gln Val
            20                  25                  30 tac gac gtg tcc tcg tgg gcc ggc ctt cat ccg ggg ggc acc gcc ccc     144
Tyr Asp Val Ser Ser Trp Ala Gly Leu His Pro Gly Gly Thr Ala Pro
        35                  40                  45 ctt ttg gcc ctc gca gga cac gac gtg acc gat gct ttc ctc gcc tac     192
Leu Leu Ala Leu Ala Gly His Asp Val Thr Asp Ala Phe Leu Ala Tyr
    50                  55                  60 cat ccc cct tcc acc gcc cgc ctc ctc cct ccc ctt tcc acc cac ctc     240
His Pro Pro Ser Thr Ala Arg Leu Leu Pro Pro Leu Ser Thr His Leu
65                  70                  75                  80 ctc ctt caa cac cac tcc gtc tcc ccc acc tcc tcc gac tac cgc tcc     288
Leu Leu Gln His His Ser Val Ser Pro Thr Ser Ser Asp Tyr Arg Ser
                85                  90                  95 ctc ctt gac aac ttc cat aaa ctt ggc ctt ttc cgc gcc agg ggc cac     336
Leu Leu Asp Asn Phe His Lys Leu Gly Leu Phe Arg Ala Arg Gly His
            100                 105                 110 act gct tac gcc acg ttc gtc atc atg ata gcg atg ttt cta gcg agt     384
Thr Ala Tyr Ala Thr Phe Val Ile Met Ile Ala Met Phe Leu Ala Ser
        115                 120                 125 gtg acc gga gtc ctc tgc agc gac aaa gca tgg gtc cat ctg gct agc     432
```

-continued

| | | | | | | | | | | | | |
|---|---|---|---|---|---|---|---|---|---|---|---|---|
| Val | Thr | Gly | Val | Leu | Cys | Ser | Asp | Lys | Ala | Trp | Val | His | Leu | Ala | Ser |
| | 130 | | | | 135 | | | | 140 | | | | | | |

| ggt | ggg | gca | atg | ggg | ttc | gcc | tgg | atc | cag | tgc | gga | tgg | ata | ggt | cac | 480 |
| Gly | Gly | Ala | Met | Gly | Phe | Ala | Trp | Ile | Gln | Cys | Gly | Trp | Ile | Gly | His |
| 145 | | | | | 150 | | | | | 155 | | | | | 160 |

| gac | tct | ggg | cat | tac | cgg | att | atg | tcc | ggt | gaa | aaa | tgg | aac | cgg | ttc | 528 |
| Asp | Ser | Gly | His | Tyr | Arg | Ile | Met | Ser | Gly | Glu | Lys | Trp | Asn | Arg | Phe |
| | | | | 165 | | | | | 170 | | | | | 175 | |

| gcg | caa | att | ctg | agc | aca | aac | tgc | ctc | cag | ggg | atc | agt | atc | ggg | tgg | 576 |
| Ala | Gln | Ile | Leu | Ser | Thr | Asn | Cys | Leu | Gln | Gly | Ile | Ser | Ile | Gly | Trp |
| | | | 180 | | | | | 185 | | | | | 190 | | |

| tgg | aag | tgg | aac | cac | aac | gct | cac | cac | atc | gct | tgc | aat | agc | ctg | gac | 624 |
| Trp | Lys | Trp | Asn | His | Asn | Ala | His | His | Ile | Ala | Cys | Asn | Ser | Leu | Asp |
| | | 195 | | | | | 200 | | | | | 205 | | | |

| tac | gac | ccc | gac | ctc | cag | tat | atc | cct | ttg | ctc | gtc | gtc | tcc | ccc | aag | 672 |
| Tyr | Asp | Pro | Asp | Leu | Gln | Tyr | Ile | Pro | Leu | Leu | Val | Val | Ser | Pro | Lys |
| 210 | | | | | 215 | | | | | 220 | | | | | |

| ttt | ttc | aac | tcc | ctt | act | tct | cgt | ttc | tat | gac | aag | aag | ctg | aac | ttc | 720 |
| Phe | Phe | Asn | Ser | Leu | Thr | Ser | Arg | Phe | Tyr | Asp | Lys | Lys | Leu | Asn | Phe |
| 225 | | | | | 230 | | | | | 235 | | | | | 240 |

| gac | ggt | gtg | tct | agg | ttc | ttg | gtt | tgc | tac | cag | cac | tgg | acg | ttt | tat | 768 |
| Asp | Gly | Val | Ser | Arg | Phe | Leu | Val | Cys | Tyr | Gln | His | Trp | Thr | Phe | Tyr |
| | | | | 245 | | | | | 250 | | | | | 255 | |

| ccg | gtc | atg | tgt | gtc | gct | agg | ctt | aac | atg | atc | gcg | cag | tcg | ttt | ata | 816 |
| Pro | Val | Met | Cys | Val | Ala | Arg | Leu | Asn | Met | Ile | Ala | Gln | Ser | Phe | Ile |
| | | | 260 | | | | | 265 | | | | | 270 | | |

| atg | ctc | ttc | tcg | agt | agg | gag | gtg | gcg | caa | agg | gtg | caa | ggg | att | ttc | 864 |
| Met | Leu | Phe | Ser | Ser | Arg | Glu | Val | Ala | Gln | Arg | Val | Gln | Gly | Ile | Phe |
| | | | 275 | | | | | 280 | | | | | 285 | | |

| gga | ctt | gcc | gtg | ttt | tgg | gtt | tgg | ttt | ccg | ctt | tta | ctt | tct | tgc | tta | 912 |
| Gly | Leu | Ala | Val | Phe | Trp | Val | Trp | Phe | Pro | Leu | Leu | Leu | Ser | Cys | Leu |
| 290 | | | | | 295 | | | | | 300 | | | | | |

| cct | aat | tgg | ggg | gag | agg | ata | atg | ttt | ttg | ctt | gcg | agc | tat | tcc | gtt | 960 |
| Pro | Asn | Trp | Gly | Glu | Arg | Ile | Met | Phe | Leu | Leu | Ala | Ser | Tyr | Ser | Val |
| 305 | | | | | 310 | | | | | 315 | | | | | 320 |

| acg | ggg | ata | caa | cac | gtg | cag | ttc | agc | ttg | aac | cat | ttt | tct | tcg | gac | 1008 |
| Thr | Gly | Ile | Gln | His | Val | Gln | Phe | Ser | Leu | Asn | His | Phe | Ser | Ser | Asp |
| | | | | 325 | | | | | 330 | | | | | 335 | |

| gtc | tac | gtg | ggc | ccg | cca | gta | ggt | aac | gac | tgg | ttc | aag | aaa | cag | act | 1056 |
| Val | Tyr | Val | Gly | Pro | Pro | Val | Gly | Asn | Asp | Trp | Phe | Lys | Lys | Gln | Thr |
| | | | 340 | | | | | 345 | | | | | 350 | | |

| gcg | ggg | acg | ctt | aac | ata | tcg | tgc | ccg | gcg | tgg | atg | gat | tgg | ttc | cat | 1104 |
| Ala | Gly | Thr | Leu | Asn | Ile | Ser | Cys | Pro | Ala | Trp | Met | Asp | Trp | Phe | His |
| | | | 355 | | | | | 360 | | | | | 365 | | |

| ggc | ggg | ttg | cag | ttt | cag | gtc | gag | cac | cac | ttg | ttc | ccg | cgg | atg | cct | 1152 |
| Gly | Gly | Leu | Gln | Phe | Gln | Val | Glu | His | His | Leu | Phe | Pro | Arg | Met | Pro |
| | 370 | | | | | 375 | | | | | 380 | | | | |

| agg | ggt | caa | ttt | agg | aag | att | tct | cct | ttt | gtg | agg | gat | ttg | tgt | aag | 1200 |
| Arg | Gly | Gln | Phe | Arg | Lys | Ile | Ser | Pro | Phe | Val | Arg | Asp | Leu | Cys | Lys |
| 385 | | | | | 390 | | | | | 395 | | | | | 400 |

| aaa | cac | aat | ttg | cct | tac | aat | atc | gca | tct | ttt | act | aaa | gca | aac | gtt | 1248 |
| Lys | His | Asn | Leu | Pro | Tyr | Asn | Ile | Ala | Ser | Phe | Thr | Lys | Ala | Asn | Val |
| | | | | 405 | | | | | 410 | | | | | 415 | |

| ttg | acg | ctt | atg | acg | ctg | aga | aat | aca | gcc | gtt | gag | gct | cgg | gac | ctc | 1296 |
| Leu | Thr | Leu | Met | Thr | Leu | Arg | Asn | Thr | Ala | Val | Glu | Ala | Arg | Asp | Leu |
| | | | 420 | | | | | 425 | | | | | 430 | | |

| tct | aat | ccg | atc | ccg | aag | aat | atg | gtg | tgg | gaa | gct | gtt | caa | act | ctc | 1344 |
| Ser | Asn | Pro | Ile | Pro | Lys | Asn | Met | Val | Trp | Glu | Ala | Val | Gln | Thr | Leu |
| 435 | | | | | 440 | | | | | 445 | | | | | |

| ggg | tga | | | | | | | | | | | | | | | 1350 |

Gly

<210> SEQ ID NO 2
<211> LENGTH: 449
<212> TYPE: PRT
<213> ORGANISM: Primula lutoides

<400> SEQUENCE: 2

```
Met Ala Asn Lys Ser Gln Thr Gly Tyr Ile Thr Ser Ser Glu Leu Glu
1               5                   10                  15

Thr His Asn Lys Ala Gly Asp Leu Trp Ile Ser Ile His Gly Gln Val
            20                  25                  30

Tyr Asp Val Ser Ser Trp Ala Gly Leu His Pro Gly Gly Thr Ala Pro
        35                  40                  45

Leu Leu Ala Leu Ala Gly His Asp Val Thr Asp Ala Phe Leu Ala Tyr
    50                  55                  60

His Pro Pro Ser Thr Ala Arg Leu Leu Pro Pro Leu Ser Thr His Leu
65                  70                  75                  80

Leu Leu Gln His His Ser Val Ser Pro Thr Ser Ser Asp Tyr Arg Ser
                85                  90                  95

Leu Leu Asp Asn Phe His Lys Leu Gly Leu Phe Arg Ala Arg Gly His
            100                 105                 110

Thr Ala Tyr Ala Thr Phe Val Ile Met Ile Ala Met Phe Leu Ala Ser
        115                 120                 125

Val Thr Gly Val Leu Cys Ser Asp Lys Ala Trp Val His Leu Ala Ser
    130                 135                 140

Gly Gly Ala Met Gly Phe Ala Trp Ile Gln Cys Gly Trp Ile Gly His
145                 150                 155                 160

Asp Ser Gly His Tyr Arg Ile Met Ser Gly Glu Lys Trp Asn Arg Phe
                165                 170                 175

Ala Gln Ile Leu Ser Thr Asn Cys Leu Gln Gly Ile Ser Ile Gly Trp
            180                 185                 190

Trp Lys Trp Asn His Asn Ala His His Ile Ala Cys Asn Ser Leu Asp
        195                 200                 205

Tyr Asp Pro Asp Leu Gln Tyr Ile Pro Leu Leu Val Val Ser Pro Lys
    210                 215                 220

Phe Phe Asn Ser Leu Thr Ser Arg Phe Tyr Asp Lys Lys Leu Asn Phe
225                 230                 235                 240

Asp Gly Val Ser Arg Phe Leu Val Cys Tyr Gln His Trp Thr Phe Tyr
                245                 250                 255

Pro Val Met Cys Val Ala Arg Leu Asn Met Ile Ala Gln Ser Phe Ile
            260                 265                 270

Met Leu Phe Ser Ser Arg Glu Val Ala Gln Arg Val Gln Gly Ile Phe
        275                 280                 285

Gly Leu Ala Val Phe Trp Val Trp Phe Pro Leu Leu Leu Ser Cys Leu
    290                 295                 300

Pro Asn Trp Gly Glu Arg Ile Met Phe Leu Leu Ala Ser Tyr Ser Val
305                 310                 315                 320

Thr Gly Ile Gln His Val Gln Phe Ser Leu Asn His Phe Ser Ser Asp
                325                 330                 335

Val Tyr Val Gly Pro Pro Val Gly Asn Asp Trp Phe Lys Lys Gln Thr
            340                 345                 350

Ala Gly Thr Leu Asn Ile Ser Cys Pro Ala Trp Met Asp Trp Phe His
        355                 360                 365

Gly Gly Leu Gln Phe Gln Val Glu His His Leu Phe Pro Arg Met Pro
```

```
                   370                 375                 380
Arg Gly Gln Phe Arg Lys Ile Ser Pro Phe Val Arg Asp Leu Cys Lys
385                 390                 395                 400

Lys His Asn Leu Pro Tyr Asn Ile Ala Ser Phe Thr Lys Ala Asn Val
                405                 410                 415

Leu Thr Leu Met Thr Leu Arg Asn Thr Ala Val Glu Ala Arg Asp Leu
                420                 425                 430

Ser Asn Pro Ile Pro Lys Asn Met Val Trp Glu Ala Val Gln Thr Leu
                435                 440                 445

Gly

<210> SEQ ID NO 3
<211> LENGTH: 1353
<212> TYPE: DNA
<213> ORGANISM: Primula cortusoides
<220> FEATURE:
<221> NAME/KEY: CDS
<222> LOCATION: (1)..(1353)
<223> OTHER INFORMATION: Delta-6-desaturase

<400> SEQUENCE: 3 atg gcc aac cca tca aaa aac agt tac att tcc gtc tca gac ctc aaa        48
Met Ala Asn Pro Ser Lys Asn Ser Tyr Ile Ser Val Ser Asp Leu Lys
1               5                   10                  15 acc cac aac aag ccc gga gac ctc tgg ata tcc atc cac ggc caa gtc        96
Thr His Asn Lys Pro Gly Asp Leu Trp Ile Ser Ile His Gly Gln Val
                20                  25                  30 tac gac gtc tct gcg tgg gcg cca cgc cac cct ggc ggc ctc cct ctc       144
Tyr Asp Val Ser Ala Trp Ala Pro Arg His Pro Gly Gly Leu Pro Leu
            35                  40                  45 ctc ctc tct cac ggc ggt cat gac gtc acg gat gcc ttc ctc gcc tac       192
Leu Leu Ser His Gly Gly His Asp Val Thr Asp Ala Phe Leu Ala Tyr
        50                  55                  60 cac ccc ccc tcg gtt tcc cgc ctc ctc cct tct ctc tct acc tac ctc       240
His Pro Pro Ser Val Ser Arg Leu Leu Pro Ser Leu Ser Thr Tyr Leu
65                  70                  75                  80 cgc ctc gaa aac cac tcc gtc tcc gcc ccc tcc tcc gac tac cgc acc       288
Arg Leu Glu Asn His Ser Val Ser Ala Pro Ser Ser Asp Tyr Arg Thr
                85                  90                  95 ctc ctt tcc cat ttc gac aac ctc ggc ctc ttc cac acc aag ggc cac       336
Leu Leu Ser His Phe Asp Asn Leu Gly Leu Phe His Thr Lys Gly His
                100                 105                 110 acc att ctc gcc act ttc gtc atc atg att gcc agt atc ctc ttc tgc       384
Thr Ile Leu Ala Thr Phe Val Ile Met Ile Ala Ser Ile Leu Phe Cys
            115                 120                 125 cta tgt ggg atc ttc ctc agt act agt ttc tgg gtc cac ttg gcg agc       432
Leu Cys Gly Ile Phe Leu Ser Thr Ser Phe Trp Val His Leu Ala Ser
        130                 135                 140 ggc gtc ctg att ggg ttc gcc tgg atc cag tgc ggg tgg ctc ggg cac       480
Gly Val Leu Ile Gly Phe Ala Trp Ile Gln Cys Gly Trp Leu Gly His
145                 150                 155                 160 gac tcc gga cat tac aaa ata aca tcc ggt aaa aaa tcc aac cgc ttc       528
Asp Ser Gly His Tyr Lys Ile Thr Ser Gly Lys Lys Ser Asn Arg Phe
                165                 170                 175 gct cag gtt ctg gtc gga aac tgc ttc gcg ggg att agc atc gag tgg       576
Ala Gln Val Leu Val Gly Asn Cys Phe Ala Gly Ile Ser Ile Glu Trp
                180                 185                 190 tgg aaa tgg aac cac aac gct cac cac acc tct tgc aac agc ctc gac       624
Trp Lys Trp Asn His Asn Ala His His Thr Ser Cys Asn Ser Leu Asp
            195                 200                 205
```

| | | |
|---|---|---|
| cac gac ccc gac ctc caa tac att ccc ttc ttg gtc gtt tcc tcc aag<br>His Asp Pro Asp Leu Gln Tyr Ile Pro Phe Leu Val Val Ser Ser Lys<br>210 215 220 | | 672 |
| ttc ttc act tcc atg atc act tct cgt ttc tac aac aaa aag ctg aat<br>Phe Phe Thr Ser Met Ile Thr Ser Arg Phe Tyr Asn Lys Lys Leu Asn<br>225 230 235 240 | | 720 |
| ttc aat gct atg tcg agg ttt tta gtc agc tat cag cat tgg tcg ttt<br>Phe Asn Ala Met Ser Arg Phe Leu Val Ser Tyr Gln His Trp Ser Phe<br>245 250 255 | | 768 |
| tat ccg gtt atg tgt ctc gcg agg gtc aac atg ttt ctg cag tcg ctt<br>Tyr Pro Val Met Cys Leu Ala Arg Val Asn Met Phe Leu Gln Ser Leu<br>260 265 270 | | 816 |
| gtc ttc ctt ttt ttc aat aag gag gtg caa aat agg gtt caa gag att<br>Val Phe Leu Phe Phe Asn Lys Glu Val Gln Asn Arg Val Gln Glu Ile<br>275 280 285 | | 864 |
| cta ggg ata gct gtg ttc tgg gtt tgg ttt ccg ctc gta gtt tct tcc<br>Leu Gly Ile Ala Val Phe Trp Val Trp Phe Pro Leu Val Val Ser Ser<br>290 295 300 | | 912 |
| ctt cct aat tgg ggt gag aga ata atg ttt ctg gtt gcg agc ttc tct<br>Leu Pro Asn Trp Gly Glu Arg Ile Met Phe Leu Val Ala Ser Phe Ser<br>305 310 315 320 | | 960 |
| att aca gga atc caa cag gtg cag ttt agc gta aac cat ttt tcg tcg<br>Ile Thr Gly Ile Gln Gln Val Gln Phe Ser Val Asn His Phe Ser Ser<br>325 330 335 | | 1008 |
| gat gtc tac gtc ggc cct ccg atg gaa aac gat tgg ttt gaa aaa cag<br>Asp Val Tyr Val Gly Pro Pro Met Glu Asn Asp Trp Phe Glu Lys Gln<br>340 345 350 | | 1056 |
| act gcc ggg acg ctc aac ata tcg tgc ccg acg tgg atg gat tgg ttc<br>Thr Ala Gly Thr Leu Asn Ile Ser Cys Pro Thr Trp Met Asp Trp Phe<br>355 360 365 | | 1104 |
| cat ggc ggg ttg cag ttt caa atc gag cac cac ttg ttc ccg cgg atg<br>His Gly Gly Leu Gln Phe Gln Ile Glu His His Leu Phe Pro Arg Met<br>370 375 380 | | 1152 |
| ccg agg agt caa ctt aga aag atc tct cct ttt gtt aag gat ttg tgt<br>Pro Arg Ser Gln Leu Arg Lys Ile Ser Pro Phe Val Lys Asp Leu Cys<br>385 390 395 400 | | 1200 |
| aaa aaa cat aac ttg cct tac aag atc gcg tct ttt aca acg gcc aat<br>Lys Lys His Asn Leu Pro Tyr Lys Ile Ala Ser Phe Thr Thr Ala Asn<br>405 410 415 | | 1248 |
| gtg ttg atg ctt agg act ctg aga aat gtt gct att aag gct cgg gac<br>Val Leu Met Leu Arg Thr Leu Arg Asn Val Ala Ile Lys Ala Arg Asp<br>420 425 430 | | 1296 |
| ctt tct aat ccg atc ccg aag aat ttg gtg tgg gaa gcc ttc cac aca<br>Leu Ser Asn Pro Ile Pro Lys Asn Leu Val Trp Glu Ala Phe His Thr<br>435 440 445 | | 1344 |
| cac gga taa<br>His Gly<br>450 | | 1353 |

<210> SEQ ID NO 4
<211> LENGTH: 450
<212> TYPE: PRT
<213> ORGANISM: Primula cortusoides

<400> SEQUENCE: 4

Met Ala Asn Pro Ser Lys Asn Ser Tyr Ile Ser Val Ser Asp Leu Lys
1               5                   10                  15

Thr His Asn Lys Pro Gly Asp Leu Trp Ile Ser Ile His Gly Gln Val
            20                  25                  30

Tyr Asp Val Ser Ala Trp Ala Pro Arg His Pro Gly Gly Leu Pro Leu
        35                  40                  45

```
Leu Leu Ser His Gly Gly His Asp Val Thr Asp Ala Phe Leu Ala Tyr
 50                  55                  60

His Pro Pro Ser Val Ser Arg Leu Leu Pro Ser Leu Ser Thr Tyr Leu
65                   70                  75                  80

Arg Leu Glu Asn His Ser Val Ser Ala Pro Ser Ser Asp Tyr Arg Thr
                 85                  90                  95

Leu Leu Ser His Phe Asp Asn Leu Gly Leu Phe His Thr Lys Gly His
            100                 105                 110

Thr Ile Leu Ala Thr Phe Val Ile Met Ile Ala Ser Ile Leu Phe Cys
        115                 120                 125

Leu Cys Gly Ile Phe Leu Ser Thr Ser Phe Trp Val His Leu Ala Ser
    130                 135                 140

Gly Val Leu Ile Gly Phe Ala Trp Ile Gln Cys Gly Trp Leu Gly His
145                 150                 155                 160

Asp Ser Gly His Tyr Lys Ile Thr Ser Gly Lys Lys Ser Asn Arg Phe
                165                 170                 175

Ala Gln Val Leu Val Gly Asn Cys Phe Ala Gly Ile Ser Ile Glu Trp
            180                 185                 190

Trp Lys Trp Asn His Asn Ala His His Thr Ser Cys Asn Ser Leu Asp
        195                 200                 205

His Asp Pro Asp Leu Gln Tyr Ile Pro Phe Leu Val Val Ser Ser Lys
210                 215                 220

Phe Phe Thr Ser Met Ile Thr Ser Arg Phe Tyr Asn Lys Lys Leu Asn
225                 230                 235                 240

Phe Asn Ala Met Ser Arg Phe Leu Val Ser Tyr Gln His Trp Ser Phe
                245                 250                 255

Tyr Pro Val Met Cys Leu Ala Arg Val Asn Met Phe Leu Gln Ser Leu
            260                 265                 270

Val Phe Leu Phe Phe Asn Lys Glu Val Gln Asn Arg Val Gln Glu Ile
        275                 280                 285

Leu Gly Ile Ala Val Phe Trp Val Trp Phe Pro Leu Val Val Ser Ser
    290                 295                 300

Leu Pro Asn Trp Gly Glu Arg Ile Met Phe Leu Val Ala Ser Phe Ser
305                 310                 315                 320

Ile Thr Gly Ile Gln Gln Val Gln Phe Ser Val Asn His Phe Ser Ser
                325                 330                 335

Asp Val Tyr Val Gly Pro Pro Met Glu Asn Asp Trp Phe Glu Lys Gln
            340                 345                 350

Thr Ala Gly Thr Leu Asn Ile Ser Cys Pro Thr Trp Met Asp Trp Phe
        355                 360                 365

His Gly Gly Leu Gln Phe Gln Ile Glu His His Leu Phe Pro Arg Met
    370                 375                 380

Pro Arg Ser Gln Leu Arg Lys Ile Ser Pro Phe Val Lys Asp Leu Cys
385                 390                 395                 400

Lys Lys His Asn Leu Pro Tyr Lys Ile Ala Ser Phe Thr Thr Ala Asn
                405                 410                 415

Val Leu Met Leu Arg Thr Leu Arg Asn Val Ala Ile Lys Ala Arg Asp
            420                 425                 430

Leu Ser Asn Pro Ile Pro Lys Asn Leu Val Trp Glu Ala Phe His Thr
        435                 440                 445

His Gly
450
```

```
<210> SEQ ID NO 5
<211> LENGTH: 27
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(27)
<223> OTHER INFORMATION: PCR primer

<400> SEQUENCE: 5
ggtaccatgg ccaacccatc aaaaaac                                            27

<210> SEQ ID NO 6
<211> LENGTH: 27
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(27)
<223> OTHER INFORMATION: PCR primer

<400> SEQUENCE: 6
ccttccacac acacggataa gagctcc                                            27

<210> SEQ ID NO 7
<211> LENGTH: 26
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(26)
<223> OTHER INFORMATION: PCR primer

<400> SEQUENCE: 7
ggtaccatgg ctaacaaatc tcaaac                                             26

<210> SEQ ID NO 8
<211> LENGTH: 26
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(26)
<223> OTHER INFORMATION: PCR primer

<400> SEQUENCE: 8
ctgttcaaac tctcgggtga ggagct                                             26

<210> SEQ ID NO 9
<211> LENGTH: 30
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(30)
<223> OTHER INFORMATION: PCR primer

<400> SEQUENCE: 9
ggatccacca tggccaaccc atcaaaaaac                                         30
```

```
<210> SEQ ID NO 10
<211> LENGTH: 28
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(28)
<223> OTHER INFORMATION: PCR primer

<400> SEQUENCE: 10
ccttccacac acacggataa ggtctaga                                              28

<210> SEQ ID NO 11
<211> LENGTH: 29
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(29)
<223> OTHER INFORMATION: PCR primer

<400> SEQUENCE: 11
ggatccacca tggctaacaa atctcaaac                                             29

<210> SEQ ID NO 12
<211> LENGTH: 28
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(28)
<223> OTHER INFORMATION: PCR primer

<400> SEQUENCE: 12
ctgttcaaac tctcgggtga ggtctaga                                              28

<210> SEQ ID NO 13
<211> LENGTH: 21
<212> TYPE: DNA
<213> ORGANISM: unknown
<220> FEATURE:
<223> OTHER INFORMATION: degenerate primer
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (13)..(13)
<223> OTHER INFORMATION: n is inosine
<220> FEATURE:
<221> NAME/KEY: misc_feature
<222> LOCATION: (16)..(16)
<223> OTHER INFORMATION: n is inosine

<400> SEQUENCE: 13
ggntcaygay dsnggncayt a                                                     21

<210> SEQ ID NO 14
<211> LENGTH: 23
<212> TYPE: DNA
<213> ORGANISM: unknown
<220> FEATURE:
<223> OTHER INFORMATION: degenerate primer
<220> FEATURE:
<221> NAME/KEY: misc_feature
```

-continued

```
<222> LOCATION: (6)..(6)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (15)..(15)
<223> OTHER INFORMATION: n is inosine

<400> SEQUENCE: 14
ccrtcngtrt knarngcytc cca                                              23
```

US 8,013,216 B2

METHOD FOR THE PRODUCTION OF γ-LINOLENIC ACID AND/OR STEARIDONIC ACID IN TRANSGENIC BRASSICACEAE AND LINACEAE

RELATED APPLICATIONS

This application is a national stage application (under 35 U.S.C. 371) of PCT/EP2006/010408 filed Oct. 30, 2006, which claims benefit of German application 10 2005 052 551.2 filed Nov. 2, 2005.

SUBMISSION ON COMPACT DISC

The Sequence Listing associated with this application is filed in electronic format via EFS-Web and hereby incorporated by reference into the specification in its entirety. The name of the text file containing the Sequence Listing is SequenceListing_13987_00088. The size of the text file is 24 KB, and the text file was created on Apr. 25, 2008.

FIELD OF THE INVENTION

The present invention relates to the production of γ-linolenic acid ($18:3^{\Delta 6,9,12}$) or stearidonic acid ($18:4^{\Delta 6,9,12,15}$) or γ-linolenic acid ($18:3^{\times 6,9,12}$) and stearidonic acid ($18:4^{\Delta 6,9,12,15}$) in transgenic plants of the family Brassicaceae, where the transgenic plants comprise at least 10% by weight of oleic acid based on the total fatty acid content and, as the result of the activity of the Δ6-desaturases used in the method, have an increased Δ6-$C_{18}$-fatty acid content.

The invention furthermore relates to novel nucleic acid sequences which code for the Δ6-desaturases used in the method, gene constructs comprising these nucleic acid sequences, a vector and transgenic plants comprising at least one nucleic acid sequence or a gene construct.

DESCRIPTION OF RELATED ART

Fatty acids and triglycerides have a multiplicity of applications in the food industry, in animal nutrition, in cosmetics and in the pharmacological sector. Depending on whether they are free saturated or unsaturated fatty acids or triglycerides with an increased saturated or unsaturated fatty acid content, they are suitable for a wide range of applications.

Polyunsaturated long-chain ω3-fatty acids such as eicosapentanoic acid (EPA) or docosahexaenoic acid (DPA) are important components of human nutrition as the result of the different roles which they play in health, which encompass aspects such as the development of the child's brain, the functionality of the eye, the synthesis of hormones and other signal substances, and the prevention of cardiovascular complaints, cancer and diabetes (Poulos, A Lipids 30:1-14, 1995; Horrocks, L A and Yeo Y K Pharmacol Res 40:211-225, 1999). This is why there is a demand for the production of polyunsaturated long-chain fatty acids, and specifically ω3-fatty acids.

Thus, for example, polyunsaturated fatty acids are added to baby food for increasing the nutritional value and for the unhindered development of the infant. The various fatty acids and triglycerides are obtained mostly from microorganisms such as Mortierella or from oil-producing plants such as soya, oilseed rape, sunflower and others, where they are usually generated in the form of their triacylglycerides. However, no long-chain unsaturated fatty acids are found in higher plants. The long-chain fatty acids are derived mostly from fish oil or from the fermentation of suitable algae (for example Thraustochytrium) or fungi (for example Mortierella). The free fatty acids are advantageously prepared by hydrolysis.

Whether oils with saturated or with unsaturated fatty acids are preferred depends on the intended purpose; in human nutrition, for example, lipids with unsaturated fatty acids, specifically polyunsaturated fatty acids, are preferred since they have a positive effect on the cholesterol level in the blood and therefore on the possibility of heart disease. They are employed in a variety of dietetic foodstuffs or in medicaments.

The two fatty acids γ-linolenic acid and stearidonic acid, in particular stearidonic acid, have positive effects on the skin's metabolism (for example acne, sun damage) and on delaying the skin's aging processes up to a preventative and curative effect in a wide range of inflammatory processes in the body; these positive effects have been described extensively. They are also used in the concomitant therapy of prostate and intestinal cancer and in the therapy and prevention of neurological disorders (for example dyspraxia, schizophrenia). This is why these fatty acids also play an important role in the cosmetics industry and in food additives. To date, oil which is high in γ-linolenic and stearidonic acid is mainly obtained from the genus Echium.

As the result of their positive characteristics, there has been no lack of attempts in the past to make available genes which are involved in the synthesis of fatty acids or triglycerides for the production of oils in various organisms with a modified content of unsaturated fatty acids. Thus, WO 91/13972 and its US equivalent describe a Δ9-desaturase. A delta 15-desaturase is claimed in WO 93/11245 and a Δ12-desaturase in WO 94/11516. Further desaturases are described for example in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the various desaturases have to date only been insufficiently characterized in biochemical terms since the enzymes, being membrane-bound proteins, can only be isolated and characterized with great difficulty (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently studied for enzyme activity by analyzing starting materials and products. Δ6-Desaturases are described in WO 93/06712, U.S. Pat. No. 5,614,393, U.S. Pat. No. 5,614,393, WO 96/21022, WO0021557 and WO 99/27111, and also the use for the production in transgenic organisms is described, such as in WO9846763, WO9846764, WO9846765. Here, the expression of various desaturases, such as in WO9964616 or WO9846776, and the formation of polyunsaturated fatty acids are described and claimed.

There is still a great demand for novel, more suitable genes which code for enzymes which are involved in the biosynthesis of unsaturated fatty acids and which make possible the specific production of certain fatty acids on an industrial scale without undesired secondary products being generated. When choosing biosynthesis genes, it is mainly two features which are of particular importance. Firstly, there still exists a need for improved methods of obtaining the highest possible contents of polyunsaturated fatty acids. Secondly, the enzymes employed should be highly specific for a particular substrate since, as far as this is possible, no undesired secondary products must be generated which may have adverse, or as yet unresearched, physiological effects in the application for foodstuffs.

BRIEF DESCRIPTION OF THE DRAWINGS

FIG. 1 shows gas-chromatographic analysis of yeasts which comprise the plasmid pYCort6 and which have been fed 18:2. The newly formed fatty acid is γ18:3$^{\Delta 6,9,12}$ (γ-linolenic acid=GLA).

FIG. 2 shows fatty acid pattern of yeasts that had been transformed with the construct pYLut6 and fed the fatty acid 18:3$^{\Delta 9,12,15}$. The corresponding fatty acids are identified. SDA (stearidonic acid) corresponds to 18:4$^{\Delta 6,9,12,15}$.

FIG. 3 shows gas-chromatographic analysis of the fatty acids from leaf material of Arabidopsis plants which had been transformed with the plasmid pBIN-Cort6.

FIG. 4 shows gas-chromatographic analysis of the fatty acids from leaf material of Arabidopsis plants which had been transformed with the plasmid pBIN-Lut6.

DETAILED DESCRIPTION OF THE INVENTION

To make possible a fortification of food and of feed with these specifically produced, polyunsaturated fatty acids, there is therefore a great demand for a simple, inexpensive method of producing these polyunsaturated fatty acids with the aid of enzymes which are involved in fatty acid biosynthesis and which are as specific as possible.

It was therefore an object to develop a novel method of producing γ-linolenic acid and/or stearidonic acid in a plant, which method makes possible the synthesis of these fatty acids in as specific a manner as possible. This object was achieved by the present method of producing γ-linolenic acid (18:3$^{\Delta 6,9,12}$) or stearidonic acid (18:4$^{\Delta 6,9,12,15}$) or γ-linolenic acid (18:3$^{\Delta 6,9,12}$) and stearidonic acid (18:4$^{\Delta 6,9,12,15}$) in transgenic plants of the family Brassicaceae or Linaceae, wherein the transgenic plants comprise at least 10% by weight of oleic acid based on the total fatty acid content and which comprises the following process steps:
 a) introducing a nucleic acid sequence into the oil plant which codes for a Δ6-desaturase from a *Primula* species and which preferentially utilizes, as substrate, α-linolenic acid to linolenic acid, and
 b) expression, in the transgenic plant, of the Δ6-desaturase encoded by the nucleic acid, and
 c) growing and harvesting the plants.

The transgenic oil plants of the family Brassicaceae or Linaceae advantageously comprise at least 11, 12, 33, 14 or 15% by weight of oleic acid, advantageously at least 16, 17, 18, 19 or 20% by weight of oleic acid based on the total fatty acid content, especially advantageously at least 25, 30, 35, 40, 45, 50, 55 or 60% by weight of oleic acid based on the total fatty acid content, very especially advantageously at least 61, 62, 63, 64, 65, 66, 67, 68, 69 or 70% by weight of oleic acid, based on the total fatty acid content or more. Plants which are advantageous for the method according to the invention furthermore have a preferred palmitic acid content of at least 9, 10, 11, 12, 13, 14 or 15% by weight, advantageously of 20, 21, 22, 23, 24 or 25% by weight, especially advantageously of 26, 27, 28, 29 or 30% by weight, based on the total fatty acid content. Other advantageous plants have a linoleic acid content of at least 20, 25, 30, 35, 40, 45 or 50% by weight, advantageously of 55, 60, 65, 70 or 75% by weight, based on the total fatty acid content. Other advantageous plants have an α-linolenic acid content of at least 10, 15, 20, 25 or 30% by weight, advantageously of 35, 40, 45 or 50% by weight, especially advantageously of 55, 60, 65 or 70% by weight, based on the total fatty acid content. Advantageous plants may also contain combinations of the abovementioned fatty acids, the total fatty acid content being 100% by weight.

The transgenic plants of the family Brassicaceae or Linaceae which are used in the method advantageously have a total oil content in the seed of at least 20, 25 or 30% by weight, advantageously around at least 35 or 40% by weight, especially advantageously around at least 45 or 50% by weight, very especially advantageously of at least 55% by weight, based on the total weight of the seed.

Oil crop plants which are preferred in the method produce oils, lipids and/or free fatty acids which comprise less than 4, 3, 2 or 1% by weight, advantageously less than 0.9, 0.8, 0.7, 0.6 or 0.5% by weight, especially advantageously less than 0.4, 0.3, 0.2, 0.1 or 0.09% by weight or less of myristic acid. Other advantageous oil crop plants comprise less than 5, 4 or 3% by weight of palmitic acid and/or less than 2, 1.5 or 1% by weight of stearic acid.

Besides a high oil content in the seed, advantageous oil plants should also have a low protein content in the seed. This protein content should, if possible, be less than 30, 25 or 20% by weight, advantageously less than 19, 18, 17, 16 or 15% by weight.

Plants which are suitable for the method according to the invention are, in principle, all genera of the family Brassicaceae (approximately 380 genera worldwide) with the subfamilies Arabideae, Brassiceae, Chamireae, Cremolobeae, Heliophileae, Hesperideae, Lepidieae, Prynglea, Schizopetaleaee, Sisymbrieae, Stenopetaleae and Thelypodieae or of the family Linaceae (9 genera worldwide). Plants which are preferred for the method according to the invention are genera of the families Brassicaceae or Linaceae selected from the group consisting of *Alliaria, Alyssoides, Arabis, Armoracia, Barbarea, Berteroa, Brassica, Camelina, Capsella, Cardamine, Cardaria, Cheiranthus, Crambe, Dentaria, Diplotaxis, Erophila, Erysimum, Iberis, Lepidium, Lunaria, Nasturtium, Raphanus, Rorippa, Schivereckia, Sinapis, Sisymbrium, Thlaspi, Turritis, Anisadenia, Cliococca, Durandea, Hebepetalum, Hesperolinon, Hugonia, Indorouchera, Linum, Philbornea, Radiola, Reinwardtia, Roucheria, Sclerolinon* and *Tirpitzia*.

Plants which are especially preferred for the method according to the invention are the genera and species selected from the group consisting of *Alliaria petiolata, Alyssoides utriculata, Arabis caucasica, Arabis procurrens, Arabis turrita, Armoracia rusticana, Barbarea intermedia, Barbaraea vulgaris, Berteroa incana, Brassica napus, Brassica napus* ssp. *rapifera, Brassica napus* ssp. *napus, Brassica nigra, Brassica oleracea, Brassica rapa, Brassica rapa* ssp. *oleifera, Brassica rapa* ssp. *rapa, Brassica sativus, Camelina sativa, Capselia bursa-pastoris, Cardamine amara, Cardamine bulbifera, Cardamine hirsuta, Cardamine pratensis, Cardaria draba, Cheiranthus cheiri, Crambe abyssinica, Dentaria bulbifera, Diplotaxis tenuifolia, Erophila verna, Erophila verna agg, Erysimum bicolor, Erysimum cheiranthoides, Iberis spec, Lepidium campestre, Lepidium sativum, Lepidium virginicum, Lunaria annua, Lunaria rediviva, Nasturtium officinale, Raphanus raphanistrum, Rorippa pyrenaica, Schivereckia podolica, Sinapis alba, Sinapis arvensis, Sisymbrium officinale, Thlaspi arvense, Thlaspi perfoliatum, Turritis glabra, Linumalpinum, Linum austriacum, Linum catharticum, Linum flavum, Linum grandiflorum, Linum hirsutum, Linum leonii, Linum maritimum, Linum ockendonii, Linum perenne, Linum tenuifolium, Linum viscosum* and *Linum usitatissimum*.

Plants which are especially advantageously used in the method are plants selected among the group of the oil plants selected from the group consisting of the genera and species *Brassica campestris, Brassica napus, Brassica rapa, Brassica juncea, Cameina sativa, Crambe abyssinica* and *Linum*

*usitatissimum*. Plants which are very especially preferred in the method according to the invention are the genera and species *Brassica campestris, Brassica napus, Brassica rapa, Brassica juncea, Camelina sativa* and *Linum usitatissimum*.

Nucleic acid sequences which are advantageously used in the method according to the invention are those which code for a Δ6-desaturase from *Primula* species, selected from the group consisting of:
  a) a nucleic acid sequence with the sequence shown in SEQ ID NO: 1 or SEQ ID NO: 3,
  b) nucleic acid sequences which, as the result of the degeneracy of the genetic code, can be derived from the amino acid sequence shown in SEQ ID NO: 2 or SEQ ID NO: 4, or
  c) derivatives of the nucleic acid sequence shown in SEQ ID NO: 1 or SEQ ID NO: 3 which code for polypeptides which have at least 40% homology at the amino acid level with SEQ ID NO: 2 or SEQ ID NO: 4 and which have a Δ6-desaturase activity.

In the method of expressing the nucleic acid sequences mentioned under (a), (b) and (c), these nucleic acid sequences are advantageously linked operably with a promoter or terminator or promoter and terminator.

In the method according to the invention for the production of γ-linolenic acid and/or stearidonic acid in a transgenic plant of the family Brassicaceae or Linaceae, the Δ6-$C_{18}$-fatty acid content is, as a result of the activity of the enzyme Δ6-desaturase, increased over the nontransgenic initial plant (wild type). The term "increased" is understood as meaning, for the purposes of the invention, that the Δ6-$C_{18}$-fatty acid content (γ-linolenic acid and/or stearidonic acid content) is increased over the wild type by at least 25, 30, 35, 40, 45 or 50%, advantageously by at least 55, 60, 65, 70, 75, 80, 85, 90, 95 or 100%, especially advantageously by at least 105, 110, 115, 120, 125, 130, 135, 140, 145 or 150% or more.

The Δ6-desaturase used in the method advantageously has a substrate specificity for α-linolenic acid which is more than 20 times, advantageously more than 25, 30, 35 or 40 times higher than the substrate specificity for linoleic acid. In an especially advantageous embodiment of the invention, the Δ6-desaturase has an exclusive substrate specificity for α-linolenic acid, that is to say that the enzyme only recognizes α-linolenic acid, but not linoleic acid, as its substrate. This results in an advantageous synthesis of unsaturated fatty acids of the ω3-synthetic pathway, while linoleic acid, being the starting substrate of the ω6-synthetic pathway, is not converted by the desaturase.

In the method, γ-linolenic acid and/or stearidonic acid, being products of the enzymatic activity of the enzyme Δ6-desaturase, are advantageously accumulated in the seed of the oil plants.

The fatty acids γ-linolenic acid and/or stearidonic acid which are produced in the method are advantageously generated as free fatty acids or, preferably, in the form of esters, preferably in the form of triglycerides.

A further subject matter of the invention is a method of producing triglycerides with an increased content in the unsaturated fatty acids γ-linolenic acid and/or stearidonic acid by incubating triglycerides with saturated or unsaturated or saturated and unsaturated fatty acids with at least the protein which is encoded by the sequence SEQ ID NO: 1 or SEQ ID NO: 3. The method is advantageously carried out in the presence of compounds which are capable of accepting or donating reduction equivalents. Thereafter, the fatty acids can be liberated from the triglycerides.

Plants which are advantageously used in the method according to the invention are transgenic plants of the family Brassicaceae or Linaceae. These plants comprise the polyunsaturated fatty acids γ-linolenic acid and/or stearidonic acid which are synthesized in the method according to the invention and can advantageously be marketed directly without it being necessary for the oils, lipids or fatty acids which have been synthesized to be isolated. Plants in the method according to the invention are intact plants and all plant plants, plant organs or plant parts such as leaf, stalk, seed, root, tuber, anthers, fibers, root hairs, stems, embryos, calli, cotyledons, petioles, crop material, plant tissue, reproductive tissue, cell cultures which are derived from the transgenic plant and/or which can be used for generating the transgenic plant. In this context, the seed comprises all parts of the seed such as the seed coats, epidermal cells and seed cells, endosperm or embryonic tissue. However, the compounds produced in the method according to the invention can also be isolated from the plants in the form of their oils, fat, lipids and/or free fatty acids. Polyunsaturated fatty acids produced by this method can be harvested by harvesting the plants either from the culture in which they grow or from the field. This can be accomplished via pressing or extracting the plant parts, preferably the plant seeds. In this context, the oils, fats, lipids and/or free fatty acids can be obtained by what is known as cold beating or cold pressing, without supplying heat. The plant parts, specifically the seeds, are beforehand comminuted, steam-treated or toasted in order to facilitate their disruption. The seeds which have been pretreated thus can subsequently be pressed or else extracted with solvents such as warm hexane. The solvent is subsequently removed. In this manner, more than 96% of the compounds produced in the method can be isolated. The resulting products are subsequently processed further, i.e. refined. Here, for example the plant mucilages and turbid matter are first removed. What is known as degumming can be performed enzymatically or, for example, chemico-physically by adding acid such as phosphoric acid. The free fatty acids are subsequently removed by treatment with a base, for example sodium hydroxide solution. The resulting product is washed thoroughly with water to remove the alkali remaining in the product and then dried. To remove the coloring matter which still remains in the product, the products are bleached, for example using bleaching earth or active charcoal. At the end, the product is deodorized, for example by using steam.

The PUFAs produced in the method are advantageously generated in the plants in the form of their oils, lipids or fatty acids or fractions of these.

A further embodiment according to the invention is the use of the oil, lipid, the fatty acids and/or the fatty acid composition which have been prepared by mixing the produced oils, lipids or fatty acids with other animal, microbial or vegetable oils in foods, feeds, cosmetics or pharmaceuticals.

The term "oil", "lipid" or "fat" is understood as meaning a fatty acid mixture which comprises unsaturated, saturated, preferably esterified fatty acid(s). It is preferred that the oil, lipid or fat has a high content of polyunsaturated free or, advantageously, esterified fatty acid(s), in particular linoleic acid, α-linolenic acid, γ-linolenic acid and/or stearidonic acid. The amount of unsaturated esterified fatty acids is preferably approximately 30% by weight, with an amount of 50% by weight being more preferred and an amount of 60, 70, 80% by weight or more being even more preferred. For identification purposes, it is possible, for example, to determine the amount of fatty acid by gas chromatography after converting the fatty acids into the methyl esters by means of transesterification. The oil, lipid or fat can comprise various other saturated or unsaturated fatty acids, for example palmitic acid, palmitoleic acid, stearic acid, oleic acid and the like. The amount of the various fatty acids in the oil or fat can vary in particular as a function of the initial organism.

The polyunsaturated fatty acids produced in the method are, for example, sphingolipids, phosphoglycerides, lipids, glycolipids, phospholipids, monoacylglycerol, diacylglycerol, triacylglycerol or other fatty acid esters.

The fatty acids present can be liberated from the polyunsaturated fatty acids produced in the method according to the invention for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification with, for example, $H_2SO_4$. However, the fatty acids can also be liberated directly without the above-described processing.

The oils, lipids or fatty acids can be obtained in the customary manner from the plants after they have been cultured. To this end, the plants and/or their seeds can, after the harvest, first be disrupted or else used directly. The oils, lipids and/or fatty acids are advantageously extracted with suitable solvents such as apolar solvents such as hexane or ethanol, isopropanol or mixtures such as hexane/isopropanol, phenol/chloroform/isoamyl alcohol at temperatures of between 0° C. to 80° C., preferably between 20° C. to 50° C. As a rule, the biomass is extracted with an excess of solvent, for example in a 1:4 excess of solvent over biomass. The solvent is subsequently removed, for example via distillation. The extraction can also be accomplished using supercritical $CO_2$. After the extraction, the remainder of the biomass can be removed by, for example, filtration.

The crude oil thus obtained can subsequently be purified further, for example by removing turbidity via treatment with polar solvents such as acetone or chloroform, followed by filtration or centrifugation. A further purification via columns is also possible.

To obtain the free fatty acids from the triglycerides, the latter are hydrolyzed in the customary manner as has been described.

The oils, lipids and/or free fatty acids obtained thus in the method, or the triglycerides with an increased γ-linolenic acid and/or stearidonic acid content which have been produced by the abovementioned methods, can be used for preparing foods, feeds, cosmetics or pharmaceuticals. To this end, they are added to the foods, the feed, the cosmetics or pharmaceuticals in customary amounts. In another embodiment, the oils, lipids and/or free fatty acids or the triglycerides with an increased γ-linolenic acid and/or stearidonic acid content are mixed with other animal, microbial or vegetable oils, lipids or fatty acids to give fatty acid compositions. The latter can be added in customary amounts to foods, to the feed, the cosmetics or pharmaceuticals.

The abovementioned methods advantageously make possible the synthesis of fatty acids or triglycerides with an increased content of fatty acids with Δ6-double bonds, advantageously C18-fatty acids.

The abovementioned method advantageously makes possible the synthesis of fatty acids or triglycerides with an increased content of fatty acids with Δ6-double bonds, where, preferentially, linoleic acid and/or α-linolenic acid, advantageously only α-linolenic acid, is utilized as the substrate for the reaction of the enzyme Δ6-desaturase. Thus, the abovementioned method advantageously makes possible in particular the synthesis of γ-linolenic acid and/or stearidonic acid, preferably of stearidonic acid alone. This specific substrate specificity of the Δ6-desaturase according to the invention differs advantageously from the substrate specificities of the prior-art Δ6-desaturases.

The invention therefore furthermore relates to isolated nucleic acid sequences which code for polypeptides with Δ6-desaturase activity and where the encoded Δ6-desaturase preferentially utilizes α-linolenic acid to linoleic acid, selected from the group consisting of:
 a) a nucleic acid sequence with the sequence shown in SEQ ID NO: 1 or SEQ ID NO: 3,
 b) nucleic acid sequences which, as the result of the degeneracy of the genetic code, can be derived from the amino acid sequence shown in SEQ ID NO: 2 or SEQ ID NO: 4, or
 c) derivatives of the nucleic acid sequence shown in SEQ ID NO: 1 which code for polypeptides which have at least 95% homology at the amino acid level with SEQ ID NO: 2 or derivatives of the nucleic acid sequence shown in SEQ ID NO: 3 which code for polypeptides which have at least 80% homology at the amino acid level with SEQ ID NO: 4 and which have a Δ6-desaturase activity.

The Δ6-desaturases found differ from the described Δ6-desaturases by very different nucleotide and amino acid sequences. The *Primula* sequence of *P. cortusoides* has 78% similarity at the amino acid level with the prior-art Δ6-desaturase sequences. The *P. lutoides* Δ6-desaturase sequence according to the invention has 92% similarity at the amino acid level with the prior-art sequences.

The nucleic acid sequences according to the invention advantageously derive from a plant, preferably from a plant of the family Primulaceae, especially preferably from the genus *Primula*, very especially preferably from the genera and species *Primula cortusoides* or *Primula lutoides*.

For the purposes of the invention, the term "Δ6-desaturase" comprises proteins which are involved in the desaturation of fatty acids, advantageously of fatty acids which have a double bond at the 9-position of the fatty acid chain, and of their homologues, derivatives or analogues.

In a further embodiment, derivatives of the nucleic acid molecule according to the invention represented in SEQ ID NO: 1 or SEQ ID NO: 3 code for proteins with at least 80%, 81%, 82%, 83%, 84%, 85%, 86%, 87%, 88%, 89% or 90%, advantageously at least 91% or 92%, preferably at least 93% or 94% and more preferably at least 95% or 96% and most preferably at least approximately 97%, 98%, 99% or more homology (=identity) with the complete amino sequence SEQ ID NO: 2 or SEQ ID NO: 4. The homology was calculated over the entire amino acid or nucleic acid sequence region. The programs used for the sequence alignments were the program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which form part of the GCG software packet [Genetics Computer Group, 575 Science Drive, Madison, Wis., USA 53711 (1991)]. The values for the sequence homologies which are stated above in percent were calculated using the program GAP over the entire sequence region, with the following settings: Gap Weight: 8, Length Weight: 2, Average Match: 2.912 and Average Mismatch: −2.003.

The invention furthermore comprises nucleic acid molecules which differ from a nucleic acid sequence shown in SEQ ID NO: 1 or SEQ ID NO: 3 (and parts thereof) as the result of the degeneracy of the genetic code and which thus code for the same Δ6-desaturase as the one encoded by the nucleotide sequence shown in SEQ ID NO: 1 or SEQ ID NO: 3.

In addition to the Δ6-desaturase nucleotide sequence shown in SEQ ID NO: 1 or SEQ ID NO: 3, the skilled worker recognizes that DNA sequence polymorphisms may exist in a population which lead to modifications in the amino acid sequences of the Δ6-desaturase. These genetic polymorphisms in the Δ6-desaturase gene can exist between individuals within one population as the result of natural variation. These natural variants usually bring about a variance of 1 to 5% in the nucleotide sequence of the Δ6-desaturase gene. All of these nucleotide variations, and resulting amino acid polymorphisms, in the Δ6-desaturase which are the result of natural variation and which do not modify the functional activity of the Δ6-desaturase are to be covered by the scope of the invention.

The nucleic acid sequence according to the invention (or fragments thereof) can advantageously be used for isolating further genomic sequences by homology screening.

The abovementioned derivatives can be isolated for example from other organisms eucaryotic organisms such as plants such as, specifically, mosses, dinoflagellates or fungi. The nucleic acids according to the invention and derivatives can advantageously be isolated from plants.

Allelic variants comprise, in particular, functional variants which are obtainable from the sequence shown in SEQ ID NO: 1 or SEQ ID NO: 3 by deletion, insertion or substitution of nucleotides, the enzymatic activity of the derived proteins which are synthesized being retained.

Starting from the DNA sequences described in SEQ ID NO: 1 or SEQ ID NO: 3 or parts of these sequences, such DNA sequences can be isolated from other eucaryotes, such as, for example, those mentioned above, for example using customary hybridization methods or the PCR technology. These DNA sequences hybridize under standard conditions with the abovementioned sequences. For hybridization use is advantageously made of, for example, short oligonucleotides of the conserved regions which can be determined by comparisons with other desaturase genes in a manner known to those skilled in the art. The histidine box sequences are advantageously employed. However, longer fragments of the nucleic acids according to the invention or the complete sequences may also be used for hybridization. Depending on the nucleic acid employed: oligonucleotide, longer fragment or complete sequence, or depending on which type of nucleic acid, DNA or RNA, is used for hybridization these standard conditions vary. Thus, for example, the melting temperatures of DNA:DNA hybrids are approximately 10° C. lower than those of DNA:RNA hybrids of the same length.

By standard conditions is meant, for example, depending on the nucleic acid in question temperatures between 42° C. and 58° C. in an aqueous buffer solution having a concentration of between 0.1 and 5×SSC (1×SSC=0.15 M NaCl, 15 mM sodium citrate, pH 7.2) or additionally in the presence of 50% formamide, such as by way of example 42° C. in 5×SSC, 50% formamide. Hybridization conditions for DNA:DNA hybrids are advantageously 0.1×SSC and temperatures between approximately 20° C. and 45° C., preferably between approximately 30° C. and 45° C. For DNA:RNA hybrids the hybridization conditions are advantageously 0.1× SSC and temperatures between approximately 30° C. and 55° C., preferably between approximately 45° C. and 55° C. These temperatures specified for the hybridization are melting temperature values calculated by way of example for a nucleic acid having a length of approximately 100 nucleotides and a G+C content of 50% in the absence of formamide. The experimental conditions for DNA hybridization are described in relevant genetics textbooks such as by way of example Sambrook et al., "Molecular Cloning", Cold Spring Harbor Laboratory, 1989, and may be calculated by formulae known to those skilled in the art, for example as a function of the length of the nucleic acids, the nature of the hybrids or the G+C content. Those skilled in the art may draw on the following textbooks for further information on hybridization: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

Furthermore, by derivatives is meant homologues of the sequences SEQ ID NO: 1 or SEQ ID NO: 3, for example eucaryotic homologues, truncated sequences, single-stranded DNA of the encoding and nonencoding DNA sequence or RNA of the encoding and nonencoding DNA sequence.

In addition, by homologues of the sequences SEQ ID NO: 1 and SEQ ID NO: 3 is meant derivatives such as by way of example promoter variants. These variants may be modified by one or more nucleotide exchanges, by insertion(s) and/or deletion(s) without, however, adversely affecting the functionality or efficiency of the promoters. Furthermore, the promoters can have their efficiency increased by altering their sequence or be completely replaced by more effective promoters even of foreign organisms.

By derivatives is also advantageously meant variants whose nucleotide sequence has been altered in the region from −1 to −2000 upstream of the start codon in such a way that gene expression and/or protein expression is modified, preferably increased. Furthermore, by derivatives is also meant variants which have been modified at the 3' end.

The nucleic acid sequences according to the invention which code for a Δ6-desaturase may be produced by synthesis or obtained naturally or comprise a mixture of synthetic and natural DNA components as well as consist of various heterologous Δ6-desaturase gene segments from different organisms. In general, synthetic nucleotide sequences are produced with codons which are preferred by the corresponding host organisms, plants for example. This usually results in optimum expression of the heterologous genes. These codons preferred by plants may be determined from codons having the highest protein frequency which are expressed in most of the plant species of interest. An example concerning *Corynebacterium glutamicum* is provided in: Wada et al. (1992) Nucleic Acids Res. 20:2111-2118. Carrying out such experiments can be carried out using standard methods and are known to an expert in this field.

Functionally equivalent sequences which code for the Δ6-desaturase gene are those derivatives of the sequence according to the invention which despite a differing nucleotide sequence still possess the desired functions, that is to say the essential enzymatic activity and specific selectivity of the proteins. Thus, functional equivalents include naturally occurring variants of the sequences described herein as well as artificial ones, e.g. artificial nucleotide sequences adapted to the codon use of a plant which have been obtained by chemical synthesis.

In addition, artificial DNA sequences are suitable, provided, as described above, they mediate the desired property, for example an increase in the content of Δ6-double bonds in fatty acids, oils or lipids in the plant by overexpression of the Δ6-desaturase gene(s) in crop plants. Such artificial DNA sequences can exhibit Δ6-desaturase activity, for example by back-translation of proteins constructed by means of molecular modeling, or be determined by in vitro selection. Possible techniques for in vitro evolution of DNA to modify or improve the DNA sequences are described in Patten, P. A. et al., Current Opinion in Biotechnology 8, 724-733 (1997) or in Moore, J. C. et al., Journal of Molecular Biology 272, 336-

347 (1997). Particularly suitable are coding DNA sequences which are obtained by back-translation of a polypeptide sequence in accordance with the codon use specific to the host plant. A person skilled in the art who is familiar with the methods of plant genetics can easily determine the specific codon use by computer analyses of other known genes of the plant to be transformed.

Other suitable equivalent nucleic acid sequences which may be mentioned are sequences that encode fusion proteins, a component of the fusion protein being Δ6-desaturase polypeptide or a functionally equivalent part thereof. The second part of the fusion protein can be, for example, another polypeptide having enzymatic activity or an antigenic polypeptide sequence by means of which it is possible to detect Δ6-desaturase expression (e.g. myc tag or his tag). Preferably, however, this is a regulatory protein sequence, such as by way of example a signal sequence for the ER, which directs the Δ6-desaturase protein to the desired point of action.

The isolated nucleic acid sequences according to the invention are advantageously derived from a plant such as a monocotyledonous or dicotyledonous plant. The nucleic acid sequences are preferably derived from the family Primulaceae, as described above.

Advantageously, the Δ6-desaturase genes in the method according to the invention may be combined with other genes for fatty acid biosynthesis. Examples of such genes are the acyltransferases, other desaturases or elongases. For in vivo and especially in vitro synthesis, the combination with e.g. NADH cytochrome B5 reductases which can accept or donate reduction equivalents is advantageous.

In principle, all genes of the fatty acid or lipid metabolism can be combined with the Δ6-desaturase(s) according to the invention [for the purposes of the present application, the plural is to encompass the singular and vice versa] for preparing γ-linolenic acid and/or stearidonic acid in the method. Advantageously, genes of the fatty acid or lipid metabolism are selected from the group consisting of acyl-CoA dehydrogenase(s), acyl-ACP[=acyl carrier protein] desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacyiglycerol lipases, allene oxide synthases, hydroperoxide lyases or fatty acid elongase(s). Especially preferably, genes are selected from the group consisting of Δ4-desaturases, Δ5-desaturases, Δ9-desaturases, Δ12-desaturases, Δ6-elongases or Δ5-elongases in combination with the abovementioned genes for the Δ6-desaturase(s), it being possible to use individual genes or a plurality of genes in combination.

The invention furthermore relates to proteins which are encoded by the nucleic acid sequences according to the invention.

By the proteins (=polypeptides or amino acid sequences) according to the invention, there are understood proteins which comprise an amino acid sequence shown in the sequences SEQ ID NO: 2 and SEQ ID NO: 4 or a sequence obtainable therefrom by substitution, inversion, insertion or deletion of one or more amino acid groups, the enzymatic activities of the proteins shown in SEQ ID NO: 2 and SEQ ID NO: 4 being retained or not substantially reduced. By "not substantially reduced" there are meant all enzymes which still exhibit at least 10%, preferably 20%, particularly preferably 30%, of the enzymatic activity of the initial enzyme. In doing this, for example, certain amino acids may be replaced by others having similar physicochemical properties (space filling, basicity, hydrophobicity, etc.). For example, arginine residues are exchanged for lysine residues, valine residues, for isoleucine residues or aspartic acid residues for glutamic acid residues. However, one or more amino acids may also be swapped in sequence, added or removed, or a plurality of these measures may be combined with one another.

By derivatives is also meant functional equivalents which in particular also contain natural or artificial mutations of an originally isolated sequence encoding Δ6-desaturase which continue to exhibit the desired function, that is whose enzymatic activity and substrate selectivity is not substantially reduced. Mutations comprise substitutions, additions, deletions, exchanges or insertions of one or more nucleotide residues. Thus, for example, the present invention also encompasses those nucleotide sequences which are obtained by modification of the Δ6-desaturase nucleotide sequence. The aim of such a modification may be, e.g., to further delimit the encoding sequence contained therein or also, e.g., to insert further cleavage sites for restriction enzymes. Functional equivalents are also those variants whose function by comparison with the initial gene or gene fragment is weakened (=not substantially reduced) or reinforced (=enzyme activity higher than the activity of the initial enzyme, that is activity is higher than 100%, preferably higher than 110%, particularly preferably higher than 130%).

Here, the nucleic acid sequence may, for example, advantageously be a DNA or cDNA sequence. Coding sequences which are for insertion into a gene construct according to the invention are, for example, those which code for a Δ6-desaturase with the sequences described above and lend the host the ability to overproduce fatty acids, oils or lipids having double bonds in the Δ6 position, it being advantageous when ω3 fatty acids having at least four double bonds are produced during this process. These sequences may be of homologous or heterologous origin.

The gene construct (=expression cassette, nucleic acid construct or fragment) according to the invention is taken to mean the sequences specified in SEQ ID NO: 1 and SEQ ID NO: 3 which result from the genetic code and which were operably linked with one or more regulatory signals advantageously to increase the gene expression and which control the expression of the coding sequence in the host cell. These regulatory sequences should allow the selective expression of the genes and the protein expression. Depending on the host plant, this may mean, for example, that the gene is expressed and/or overexpressed only after induction or that it is expressed and/or overexpressed immediately. Examples of these regulatory sequences are sequences to which inductors or repressors bind and in this way regulate the expression of the nucleic acid. In addition to these new regulation sequences or instead of these sequences the natural regulation of these sequences ahead of the actual structural genes may still be present and optionally have been genetically modified so that natural regulation was switched off and the expression of the genes increased. However, the gene construct can also be simpler in construction, that is no additional regulation signals have been inserted ahead of the nucleic acid sequence or derivatives thereof and the natural promoter with its regulation has not been removed. Instead, the natural regulatory sequence was mutated in such a way that no further regulation ensues and/or the gene expression is heightened. These modified promoters in the form of part sequences (=promoter containing parts of the nucleic acid sequences according to the invention) can also be brought on their own ahead of the natural gene to increase the activity. In addition, the gene construct may advantageously also comprise one or more so-called enhancer sequences operably linked to the promoter which allow an enhanced expression of the nucleic acid sequence. At the 3' end of the DNA sequences additional advantageous sequences may also be inserted, such as further regulatory elements or terminators. The Δ6-desaturase gene may be present in one or more copies in the expression cassette (=gene construct).

As described above, the regulatory sequences or factors can preferably positively influence, and thus increase, the gene expression of the genes introduced. Thus, enhancement of the regulatory elements advantageously on the transcription level may be effected by using strong transcription signals such as promoters and/or enhancers. However, in addition strong enhancement of translation is also possible, for example by improving the stability of the mRNA.

Suitable promoters in the expression cassette are, in principle, all promoters which can control the expression of foreign genes in organisms, advantageously in plants or fungi. Use is preferably made in particular of plant promoters or promoters derived from a plant virus. Advantageous regulatory sequences for the method according to the invention are found for example in promoters such as cos, tac, trp, tet, trp-tet, lpp, lac, lpp-lac, lacI$^{q-}$, T7, T5, T3, gal, trc, ara, SP6, λ-$P_R$ or in λ-$P_L$ promoters which are employed advantageously in gram-negative bacteria. Other advantageous regulatory sequences are present, for example, in the gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], SSU, OCS, lib4, STLS1, B33, nos (=Nopalin Synthase Promoter) or in the ubiquintin promoter. The expression cassette may also comprise a chemically inducible promoter by means of which the expression of the exogenous Δ6-desaturase gene in the organisms can be controlled advantageously in the plants at a particular time. Advantageous plant promoters of this type are, for example, the PRP1 promoter [Ward et al., Plant. Mol. Biol. 22(1993), 361-366], a promoter inducible by benzenesulfonamide (EP 388186), a promoter inducible by tetracyclin (Gatz et al., (1992) Plant J. 2,397-404), a promoter inducible by salicylic acid (WO 95/19443), a promoter inducible by abscisic acid (EP335528) and a promoter inducible by ethanol or cyclohexanone (WO93/21334). Other examples of plant promoters are the promoter of cytosolic FBPase from potato, the ST-LSI promoter from potato (Stockhaus et al., EMBO J. 8 (1989) 2445-245), the promoter of phosphoribosyl pyrophosphate amidotransferase from *Glycine max* (see also gene bank accession number U87999) or a node-specific promoter as described in EP 249676 can advantageously be used. Particularly advantageous are especially those plant promoters which ensure expression in tissues or plant parts/organs in which fatty acid biosynthesis or the precursor stages thereof occurs, as in endosperm or in the developing embryo for example. Particularly noteworthy are advantageous promoters which ensure seed-specific expression such as, for example, the USP promoter or derivatives thereof, the LEB4 promoter, the phaseolin promoter or the napin promoter. The USP promoter, which is particularly advantageous and is cited according to the invention or its derivatives mediate very early gene expression in seed development (Baeumlein et al., Mol Gen Genet, 1991, 225 (3): 459-67). Other advantageous seed-specific promoters which may be used for monocotyledonous or dicotyledonous plants are the promoters suitable for dicots such as napin gene promoters, likewise cited by way of example, from oilseed rape (U.S. Pat. No. 5,608,152), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the legume B4 promoter (LeB4, Baeumlein et al., Plant J., 2, 2, 1992: 233-239) or promoters suitable for monocots such as the promoters the promoters of the Ipt2 or Ipt1 gene in barley (WO 95/15389 and WO 95/23230) or the promoters of the barley hordein gene, the rice glutelin gene, the rice oryzin gene, the rice prolamin gene, the wheat gliadin gene, the wheat glutelin gene, the corn zein gene, the oat glutelin gene, the sorghum kasirin gene or the rye secalin gene, which are described in WO 99/16890.

Furthermore, particularly preferred are those promoters which ensure the expression in tissues or plant parts in which, for example, the biosynthesis of fatty acids, oils and lipids or the precursor stages thereof takes place. Particularly noteworthy are promoters which ensure a seed-specific expression. Noteworthy are the promoter of the napin gene from oilseed rape (U.S. Pat. No. 5,608,152), the USP promoter from *Vicia faba* (USP=unknown seed protein, Baeumlein et al., Mol Gen Genet, 1991, 225 (3): 459-67), the oleosin gene from *Arabidopsis* (WO 98/45461), the phaseolin promoter (U.S. Pat. No. 5,504,200) or the promoter of the legumin B4 gene (LeB4; Baeumlein et al., 1992, Plant Journal, 2 (2): 233-9). Other promoters to be mentioned are that of the Ipt2 or Ipt1 gene from barley (WO 95/15389 and WO 95/23230) which mediate seed-specific expression in monocotyledonous plants.

Further promoters which are suitable for expression in plants have been described (Rogers et al. (1987) Method in Enzymol 153:253-277; Schardl et al. (1987) Gene 61:1-11; Berger et al. (1989) Proc Natl Acad Sci USA 86:8402-8406).

As described above, the gene construct (=expression cassette, nucleic acid construct) may comprise yet other genes which are to be introduced into the organisms. These genes can be subject to separate regulation or be subject to the same regulation region as the Δ6-desaturase gene. These genes are by way of example other biosynthesis genes, advantageously for fatty acid biosynthesis, such as biosynthesis genes of the fatty acid or lipid metabolism which allow an increased synthesis selected from the group consisting of acyl-CoA dehydrogenase(s), acyl-ACP[=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s). Examples which may be mentioned are the genes for the enzymes Δ15-, Δ12-, Δ9-, Δ6-, Δ5-desaturase, β-ketoacyl reductases, β-ketoacyl synthases, elongases or the various hydroxylases or acyl-ACP thioesterases. Desaturase and elongase genes are advantageously used in the nucleic acid construct. Genes which are especially advantageously used in the construct are selected from the group consisting of Δ4-desaturase, Δ5-desaturase, Δ8-desaturase, Δ9-desaturase, Δ12-desaturase, Δ5-elongase, Δ6-elongase or Δ9-elongase.

In principle, all natural promoters with their regulation sequences can be used like those named above for the expression cassette according to the invention and the method according to the invention, as described below. Over and above this, synthetic promoters may also advantageously be used.

In the preparation of an expression cassette various DNA fragments can be manipulated in order to obtain a nucleotide sequence which expediently reads in the correct direction and is equipped with a correct reading frame. To connect the DNA fragments (=nucleic acids according to the invention) to one another, adaptors or linkers may be attached to the fragments.

The promoter and the terminator regions can expediently be provided in the direction of transcription with a linker or polylinker comprising one or more restriction sites for the insertion of this sequence. Generally, the linker has 1 to 10, mostly 1 to 8, preferably 2 to 6, restriction sites. In general the size of the linker inside the regulatory region is less than 100 bp, frequently less than 60 bp, but at least 5 bp. The promoter may be both native or homologous as well as foreign or heterologous to the host organism, for example to the host plant. In the 5'-3' direction of transcription the expression cassette comprises the promoter, a DNA sequence which codes for a Δ6-desaturase gene and a region for transcription termination. Different termination regions can be substituted for one another in any desired fashion.

Furthermore, manipulations which provide suitable restriction cleavage sites or which remove excess DNA or restriction cleavage sites can be employed. Where insertions, deletions or substitutions, such as transitions and transversions, come into consideration, in vitro mutagenesis, primer repair, restriction or ligation may be used. In the case of suitable manipulations such as restriction, chewing back or filling in of overhangs for blunt ends, complementary ends of the fragments can be provided for the ligation.

For an advantageous high expression, the attachment of the specific ER retention signal SEKDEL inter alia can be of importance (Schouten, A. et al., Plant Mol. Biol. 30 (1996), 781-792); in this way the average expression level is tripled to quadrupled. Other retention signals which occur naturally in plant and animal proteins located in the ER may also be employed for the construction of the cassette.

Preferred polyadenylation signals are plant polyadenylation signals, preferably those which essentially correspond to T-DNA polyadenylation signals from *Agrobacterium tumefaciens*, in particular gene 3 of the T-DNA (octopine synthase) of the Ti plasmid pTiACH5 (Gielen et al., EMBO J. 3 (1984), 835 et seq.) or corresponding functional equivalents.

An expression cassette is produced by fusion of a suitable promoter with a suitable Δ6-desaturase DNA sequence together with a polyadenylation signal by common recombination and cloning techniques as described, for example, in T. Maniatis, E. F. Fritsch und J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

In the preparation of an expression cassette various DNA fragments can be manipulated in order to obtain a nucleotide sequence which expediently reads in the correct direction and is equipped with a correct reading frame. To connect the DNA fragments to one another, adaptors or linkers may be attached to the fragments.

The promoter and the terminator regions can expediently be provided in the direction of transcription with a linker or polylinker comprising one or more restriction sites for the insertion of this sequence. Generally, the linker has 1 to 10, mostly 1 to 8, preferably 2 to 6, restriction sites. In general the size of the linker inside the regulatory region is less than 100 bp, frequently less than 60 bp, but at least 5 bp. The promoter may be both native or homologous as well as foreign or heterologous to the host plant. In the 5'-3' direction of transcription the expression cassette comprises the promoter, a DNA sequence which codes for a Δ6-desaturase gene and a region for transcription termination. Different termination regions can be substituted for one another in any desired fashion.

In the preparation of an expression cassette various DNA fragments can be manipulated in order to obtain a nucleotide sequence which expediently reads in the correct direction and is equipped with a correct reading frame. To connect the DNA fragments to one another, adaptors or linkers may be attached to the fragments.

The promoter and the terminator regions can expediently be provided in the direction of transcription with a linker or polylinker comprising one or more restriction sites for the insertion of this sequence. Generally, the linker has 1 to 10, mostly 1 to 8, preferably 2 to 6, restriction sites. In general the size of the linker inside the regulatory region is less than 100 bp, frequently less than 60 bp, but at least 5 bp. The promoter may be both native or homologous as well as foreign or heterologous to the host plant. In the 5'-3' direction of transcription the expression cassette comprises the promoter, a DNA sequence which codes for a Δ6-desaturase gene and a region for transcription termination. Different termination regions can be substituted for one another in any desired fashion.

The DNA sequences coding for two Δ6-desaturases from *Primula cortusoides* or *Primula lutoides* comprise all the sequence characteristics needed to achieve correct localization of the site of fatty acid, lipid or oil biosynthesis. Accordingly, no further targeting sequences are needed per se. However, such a localization may be desirable and advantageous and hence artificially modified or enhanced so that such fusion constructs are also a preferred advantageous embodiment of the invention.

Especially preferred are sequences which ensure targeting into plastids. Under certain circumstances targeting into other compartments (reported in: Kermode, Crit. Rev. Plant Sci. 15, 4 (1996), 285-423) may also be desirable, e.g. into the vacuole, the mitochondrium, the endoplasmic reticulum (ER), peroxisomes, lipid structures or, due to lack of corresponding operative sequences, retention in the compartment of origin, the cytosol.

Advantageously, the nucleic acid sequences according to the invention together with at least one reporter gene are cloned into an expression cassette which is introduced into the organism via a vector or directly into the genome. This reporter gene should allow easy detectability via a growth, fluorescence, chemical, bioluminescence or resistance assay or via a photometric measurement. Examples of reporter genes which may be mentioned are antibiotic- or herbicide-resistance genes, hydrolase genes, fluorescence protein genes, bioluminescence genes, sugar or nucleotide metabolic genes or biosynthesis genes such as the Ura3 gene, the Ilv2 gene, the luciferase gene, the α-galactosidase gene, the gfp gene, the 2-desoxyglucose-6-phosphate phosphatase gene, the β-glucuronidase gene, β-lactamase gene, the neomycin phosphotransferase gene, the hygromycin phosphotransferase gene or the BASTA (=gluphosinate-resistance) gene. These genes permit easy measurement and quantification of the transcription activity and hence of the expression of the genes. In this way genome positions may be identified which exhibit differing productivity.

In a preferred embodiment an expression cassette comprises upstream, i.e. at the 5' end of the coding sequence, a promoter and downstream, i.e. at the 3' end, a polyadenylation signal and optionally other regulatory elements which are operably linked to the intervening coding sequence for the Δ6-desaturase and/or Δ6-desaturase DNA sequence. By an operable linkage is meant the sequential arrangement of promoter, encoding sequence, terminator and optionally other regulatory elements in such a way that each of the regulatory elements can fulfill its function in the expression of the coding sequence in due manner. The sequences preferred for operable linkage are targeting sequences for ensuring subcellular localization in plastids. However, if required, targeting sequences for ensuring subcellular localization in the mitochondrium, in the endoplasmic reticulum (=ER), in the nucleus, in oil bodies or other compartments may also be employed, as may be translation promoters such as the 5' leader sequence from the tobacco mosaic virus (Gallie et al., Nucl. Acids Res. 15 (1987), 8693-8711).

An expression cassette may, for example, comprise a constitutive promoter (preferably the USP or napin promoter), the gene to be expressed and the ER retention signal. For the ER retention signal the KDEL amino acid sequence (lysine, aspartic acid, glutamic acid, leucine) is preferably employed.

For expression in a procaryotic or eucaryotic host organism, for example a microorganism such as a fungus or a plant, the gene construct is advantageously inserted into a vector such as by way of example a plasmid, a phage or other DNA which makes possible optimum expression of the genes in the host organism. Examples of suitable plasmids are: in *E. coli* pLG338, pACYC184, pBR series such as e.g. pBR322, pUC series such as pUC18 or pUC19, M113mp series, pKC30, pRep4, pHS1, pHS2, pPLc236, pMBL24, pLG200, pUR290, pIN-III[113]-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667; in fungi pALS1, pIL2 or pBB116; other advantageous fungal vectors are described by Romanos, M. A. et al., (1992) "Foreign gene expression in yeast: a review", *Yeast* 8: 423-488] and by van den Hondel, C. A. M. J. J. et al. [(1991) "Heterologous gene expression in filamentous fungi" and in More Gene Manipulations in Fungi [J. W. Bennet & L. L. Lasure, eds., p. 396-428: Academic Press: San Diego] and in "Gene transfer systems and vector development for filamentous fungi" [van den Hondel, C. A. M. J. J. & Punt, P. J. (1991) in: Applied Molecular Genetics of Fungi, Peberdy, J. F. et al., eds., p. 1-28, Cambridge University Press: Cambridge]. Examples of advantageous yeast promoters are 2 μM, pAG-1, YEp6, YEp13 or pEMBLYe23. Examples of algal or plant promoters are pLGV23, pGHlac+, pBIN19, pAK2004, pVKH or pDH51 (see Schmidt, R. and Willmitzer, L., 1988). The vectors identified above or derivatives of the vectors identified above are a small selection of the possible plasmids. Further plasmids are well known to those skilled in the art and may be found, for example, in the book Cloning Vectors (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press), Ch. 6/7, pp. 71-119. Advantageous vectors are known as shuttle vectors or binary vectors which replicate in *E. coli* and *Agrobacterium*.

By vectors is meant with the exception of plasmids all other vectors known to those skilled in the art such as by way of example phages, viruses such as SV40, CMV, baculovirus, adenovirus, transposons, IS elements, phasmids, phagemids, cosmids, linear or circular DNA. These vectors can be replicated autonomously in the host organism or be chromosomally replicated, chromosomal replication being preferred.

In a further embodiment of the vector the expression cassette according to the invention may also advantageously be introduced into the organisms in the form of a linear DNA and be integrated into the genome of the host organism by way of heterologous or homologous recombination. This linear DNA may be composed of a linearized plasmid or only of the expression cassette as vector or the nucleic acid sequences according to the invention.

In a further advantageous embodiment the nucleic acid sequence according to the invention can also be introduced into an organism on its own.

If in addition to the nucleic acid sequence according to the invention further genes are to be introduced into the organism, all can be introduced into the organism together with a reporter gene in a single vector or each single gene with a reporter gene in a vector in each case it being possible for the different vectors to be introduced simultaneously or in succession.

The vector advantageously comprises at least one copy of the nucleic acid sequences according to the invention and/or the gene construct according to the invention.

By way of example the plant expression cassette can be installed in the pRT transformation vector ((a) Toepfer et al., 1993, Methods Enzymol., 217: 66-78; (b) Toepfer et al. 1987, Nucl. Acids. Res. 15: 5890 ff.).

Alternatively, a recombinant vector (=expression vector) can also be transcribed and translated in vitro, e.g. by using the T7 promoter and the T7 RNA polymerase.

Expression vectors employed in procaryotes frequently make use of inducible systems with and without fusion proteins or fusion oligopeptides, wherein these fusions can ensue in both N-terminal and C-terminal manner or in other useful domains of a protein. Such fusion vectors usually have the following purposes: i.) to increase the RNA expression rate; ii.) to increase the protein synthesis rate which can be achieved; iii.) to increase the solubility of the protein; iv.) or to simplify purification by means of a binding sequence which can be used for affinity chromatography. Proteolytic cleavage sites are also frequently introduced via fusion proteins which allows cleavage of a portion of the fusion protein and purification. Such recognition sequences for proteases recognized are, e.g. factor Xa, thrombin and enterokinase.

Typical advantageous fusion and expression vectors are pGEX [Pharmacia Biotech Inc; Smith, D. B. and Johnson, K. S. (1988) *Gene* 67: 31-40], pMAL (New England Biolabs, Beverly, Mass.) and pRIT5 (Pharmacia, Piscataway, N.J.) which contains glutathione S-transferase (GST), maltose binding protein or protein A.

Other examples of *E. coli* expression vectors are pTrc [Amann et al., (1988) *Gene* 69:301-315] and pET vectors [Studier et al., Gene Expression Technology: Methods in Enzymology 185, Academic Press, San Diego, Calif. (1990) 60-89; Stratagene, Amsterdam, The Netherlands].

Other advantageous vectors for use in yeast are pYepSec1 (Baldari, et al., (1987) *Embo J.* 6:229-234), pMFa (Kurjan and Herskowitz, (1982) *Cell* 30:933-943), pJRY88 (Schultz et al., (1987) *Gene* 54:113-123), and pYES derivatives (Invitrogen Corporation, San Diego, Calif.). Vectors for use in filamentous fungi are described in: van den Hondel, C. A. M. J. J. & Punt, P. J. (1991) "Gene transfer systems and vector development for filamentous fungi", in: Applied Molecular Genetics of Fungi, J. F. Peberdy, et al., eds., p. 1-28, Cambridge University Press: Cambridge.

Alternatively, insect cell expression vectors can also be advantageously utilized, e.g. for expression in Sf 9 cells. These are e.g. the vectors of the pAc series (Smith et al. (1983) *Mol. Cell Biol.* 3:2156-2165) and the pVL series (Lucklow and Summers (1989) *Virology* 170:31-39).

Furthermore, plant cells or algal cells can advantageously be used for gene expression. Examples of plant expression vectors may be found in Becker, D., et al. (1992) "New plant binary vectors with selectable markers located proximal to the left border", *Plant Mol. Biol.* 20: 1195-1197 or in Bevan, M. W. (1984) "Binary *Agrobacterium* vectors for plant transformation", *Nucl. Acid. Res.* 12: 8711-8721.

Further procaryotic and eucaryotic expression systems are mentioned in Chapters 16 and 17 in Sambrook et al., *Molecular Cloning: A Laboratory Manual* 2nd, ed., Cold Spring Harbor Laboratory, Cold Spring Harbor Laboratory Press, Cold Spring Harbor, N.Y., 1989.

The introduction of the nucleic acids according to the invention, of the expression cassette or of the vector into organisms, for example into plants, can, in principle, be accomplished by all methods known to those skilled in the art.

In the case of microorganisms, those skilled in the art can find appropriate methods in the textbooks by Sambrook, J. et al. (1989) Molecular cloning: A laboratory manual, Cold Spring Harbor Laboratory Press, by F. M. Ausubel et al. (1994) Current protocols in molecular biology, John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Harbor Laboratory Press or Guthrie et al. Guide to Yeast Genetics and Molecular Biology, Methods in Enzymology, 1994, Academic Press.

The transfer of foreign genes into the genome of a plant is called transformation. For this purpose, the methods described for the transformation and regeneration of plants from plant tissues or plant cells are utilized for transient or stable transformation. Suitable methods are protoplast transformation by poly(ethylene glycol)-induced DNA uptake, the biolistic method using the gene gun—referred to as the particle bombardment method, electroporation, the incubation of dry embryos in DNA—comprising solution, microinjection and gene transfer mediated by *Agrobacterium*. Said methods are described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225. The construct to be expressed is preferably cloned into a vector which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, in particular of crop plants such as, for example, tobacco plants, for example by bathing bruised leaves or leaf segments in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in eds. S. D. Kung and R. Wu, Academic Press, 1993, pp. 15-38.

In plants, the described methods for the transformation and regeneration of plants from plant tissues or plant cells are used for transient or stable transformation. Suitable methods are, as described above, mainly protoplast transformation by poly(ethylene glycol)-induced DNA uptake, the biolistic method using the gene gun, known as the "particle bombardment" method, electroporation, the incubation of dry embryos in DNA-comprising solution, and microinjection.

In addition to these "direct" transformation techniques, a transformation can also be accomplished by bacterial infection by means of *Agrobacterium tumefaciens* or *Agrobacterium rhizogenes* and transfer of suitable recombinant Ti plasmids or Ri plasmids by, or by infection with, transgenic plant viruses. The *Agrobacterium*-mediated transformation is best suited to dicotyledonous plant cells. The methods are described, for example, in Horsch R B et al. (1985) Science 225: 1229f.

If agrobacteria are used, the expression cassette is to be integrated into specific plasmids, either into a shuttle, or intermediate, vector or into a binary vector. If a Ti or Ri plasmid is to be used for the transformation, at least the right border, but in most cases the right and left border, of the Ti or Ri plasmid T-DNA is linked with the expression cassette to be introduced as flanking region.

It is preferred to use binary vectors. Binary vectors are capable of replicating both in *E. coli* and in *Agrobacterium*. As a rule, they comprise a selection marker gene and a linker or polylinker flanked by the right and left T-DNA border sequence. They can be transformed directly into *Agrobacterium* (Holsters et al. (1978) Mol Gen Genet 163:181-187). The selection marker gene permits a selection of transformed agrobacteria and is, for example, the nptII gene, which mediates resistance to kanamycin. The *Agrobacterium* which acts in this case as host organism should already comprise a plasmid with the vir region. This region is required for the transfer of the T-DNA to the plant cell. An *Agrobacterium* transformed thus can be used for the transformation of plant cells. The use of T-DNA for the transformation of plant cells has been studied and described widely (EP 120 516; Hoekema, In: The Binary Plant Vector System, Offsetdrukkerij Kanters B. V., Alblasserdam, Chapter V; An et al. (1985) EMBO J 4:277-287). Various binary vectors are known, and some of them are commercially available such as, for example, pBI101.2 or pBIN19 (Clontech Laboratories, Inc. USA).

Agrobacteria transformed by an expression vector according to the invention may likewise be used in a known manner for the transformation of plants such as test plants like Arabidopsis or crop plants such as canola, flax, or oilseed rape, e.g. by bathing bruised leaves or leaf segments in an agrobacterial solution and then culturing them in suitable media. Plants which are especially suitable for the production of γ-linolenic acid and/or stearidonic acid are plants from the families Brassicaceae or Linaceae. The genus *Brassica, Camelina* or *Linum* is especially advantageously suitable for the production of γ-linolenic acid and/or stearidonic acid with the nucleic acid sequences according to the invention, advantageously in combination with further desaturases and elongases.

Direct transformation techniques are suitable for any organism and cell type. In the case of injection or electroporation of DNA or RNA into plant cells, the plasmid used need not meet any particular requirements. It is possible to use simple plasmids, such as those of the pUC series. If intact plants are to be regenerated from the transformed cells, it is necessary for an additional selectable marker gene to be located on the plasmid.

Stably transformed cells, i.e. those which comprise the introduced DNA integrated into the DNA of the host cell, can be selected from untransformed cells when a selectable marker is part of the DNA which has been introduced. Any gene may act as marker which, for example, is capable of conferring a resistance to antibiotics or herbicides (such as kanamycin, G 418, bleomycin, hygromycin or phosphinothricin and the like) (see above). Transformed cells which express such a marker gene are capable of surviving in the presence of concentrations of a corresponding antibiotic or herbicide which kill an untransformed wild type. Examples are mentioned hereinabove and comprise, preferably, the bar gene which confers resistance to the herbicide phosphinothricin (Rathore K S et al. (1993) Plant Mol Biol 21(5):871-884), the nptII gene, which confers resistance to kanamycin, the hpt gene, which confers resistance to hygromycin, or the EPSP gene, which confers resistance to the herbicide glyphosate. The selection marker permits the selection of transformed cells from untransformed cells (McCormick et al. (1986) Plant Cell Reports 5:81-84). The plants obtained can be bred and hybridized in the customary manner. Two or more generations should be cultured in order to ensure that the genomic integration is stable and hereditary.

The abovementioned methods are described, for example, in Jenes B et al. (1993) Techniques for Gene Transfer, in: Transgenic Plants, Vol. 1, Engineering and Utilization, edited by S D Kung and R Wu, Academic Press, p. 128-143 and in Potrykus (1991) Annu Rev Plant Physiol Plant Molec Biol 42:205-225. The construct to be expressed is preferably cloned into a vector which is suitable for transforming *Agrobacterium tumefaciens*, for example pBin19 (Bevan et al. (1984) Nucl Acids Res 12:8711f).

Once a transformed plant cell has been produced, it is possible to obtain a complete plant using methods known to the skilled worker. The starting material here is, for example, callus cultures. The development of shoot and root from these as yet undifferentiated cell biomasses can be induced in the known manner. The plantlets obtained can be planted out and bred.

The skilled worker knows such methods for regenerating plant parts and intact plants from plant cells. Methods which are used for these purposes are, for example, methods described by Fennell et al. (1992) Plant Cell Rep. 11: 567-570; Stoeger et al (1995) Plant Cell Rep. 14:273-278; Jahne et al. (1994) Theor Appl Genet 89:525-533. Other suitable methods can be found in the abovementioned publications by S. D. Kung and R. Wu, Potrykus or Höfgen and Willmitzer.

Transgenic organisms or host organisms for the nucleic acid according to the invention, the gene constructs or the vector which are suitable in principle are, advantageously, all plants of the families Brassicaceae or Linaceae which are capable of synthesizing fatty acids, specifically unsaturated fatty acids, and/or which are suitable for the expression of recombinant genes. Examples which may be mentioned are plants such as *Arabidopsis*, oilseed rape, *Camelina*, mustard or flax. Plants which are naturally capable of synthesizing substantial amounts of oils are preferred.

A transgenic plant for the purposes of the invention is understood as meaning that the nucleic acids used in the method are not at their natural locus in the genome of the plant, it being possible for the nucleic acids to be expressed homologously or heterologously. However, transgenic also means that, while the nucleic acids according to the invention are at their natural position in the genome of the plant, the sequence has been modified with regard to the natural sequence, and/or that the regulatory sequences of the natural sequences have been modified. Transgenic is preferably understood as meaning the expression of the nucleic acids according to the invention at a non-natural locus in the genome, i.e. homologous or, preferably, heterologous expression of the nucleic acids takes place.

"Transgenic" thus means for example with regard to a nucleic acid sequence, a gene construct or a vector comprising a nucleic acid sequence which codes for Δ6-desaturase or its derivatives, or an organism transformed with this nucleic acid sequence, an expression cassette or a vector, all those constructs which have come to pass as the result of genetic engineering methods in which either a) the Δ6-desaturase nucleic acid sequence, or
b) a genetic control sequence which is operably linked with the Δ6-desaturase nucleic acid sequence, for example a promoter, or
c) (a) and (b)

are not located in their natural genetic environment or have been modified by genetic engineering methods, it being possible for the modification to be, for example, a substitutions, additions, deletions, inversion or insertions of one or more nucleotide residues. Natural genetic environment means the natural chromosomal locus in the organism of origin, or the existence in a genomic library. In the case of a genomic library, the natural genetic environment of the nucleic acid sequence is preferably retained at least in part. The environment flanks the nucleic acid sequence at least on one side and has a sequence length of at least 50 bp, preferably at least 500 bp, especially preferably at least 1000 bp, very especially preferably at least 5000 bp.

The invention furthermore relates to the use of an expression cassette comprising DNA sequences coding for a Δ6-desaturase gene, or DNA sequences hybridizing thereto, for the transformation of plant cells, plant tissues or plant parts. The purpose of their use is to increase the content of fatty acids, oils or lipids with an increased content of and double bonds in the Δ6-position.

In this context, and depending on the choice of the promoter, the expression of the Δ6-desaturase gene can be effected specifically in the leaves, in the seeds, the tubers or other parts of the plant. The present invention furthermore relates to such transgenic plants which overproduce fatty acids, oils or lipids with Δ6-double bonds, to their propagataion material, and to their plant cells, plant tissue or plant parts. A preferred subject matter according to the invention are transgenic plants of the families Brassicaceae or Linaceae comprising a nucleic acid sequence according to the invention, a gene construct according to the invention or a vector according to the invention.

Within the scope of the present invention, increasing the content of fatty acids, oils or lipids with Δ6-double bonds means, for example, the artificially acquired ability of an increased biosynthetic performance by functional overexpression of the Δ6-desaturase gene(s) (for the purposes of the invention, the singular is also to encompass the plural and vice versa) in the transgenic plants according to the invention over the initial plants which have not been the subject of modification by genetic engineering, at least for the duration of at least one plant generation.

The location of the biosynthesis of fatty acids, oils or lipids, for example, is generally the seed or cell layers of the seed, so that a seed-specific expression of the Δ6-desaturase gene is meaningful. However, it is obvious that the biosynthesis of fatty acids, oils or lipids need not be restricted to the seed tissue, but may also take place in a tissue-specific manner in all remaining parts of the plant, for example in epidermal cells or in the tubers.

Moreover, constitutive expression of the exogenous Δ6-desaturase gene is advantageous. However, inducible expression may also appear desirable, on the other hand.

The expression efficacy of the Δ6-desaturase gene can be determined for example in vitro by shoot-meristem propagation. Moreover, an expression of the Δ6-desaturase gene which is modified in terms of level and extent, and the effect of such an expression on the fatty acid, oil or lipid biosynthetic performance can be tested in greenhouse experiments, using test plants.

The invention furthermore relates to:
methods of transforming a plant from the family Brassicaceae or Linaceae, which comprises introducing expression cassettes according to the invention comprising a Δ6-desaturase gene sequence from Primulaceae, or DNA' sequences hybridizing thereto, into a plant cell, into callus tissue, into an intact plant or into plant protoplasts.

The use of a Δ6-desaturase DNA gene sequence, or of DNA sequences hybridizing thereto, for the generation of plants with an increased content of fatty acids, oils or lipids with Δ6-double bonds as the result of the expression of this Δ6-desaturase DNA sequence in plants.

Proteins comprising the amino acid sequences shown in SEQ ID NO: 2 or SEQ ID NO: 4.

The use of the proteins with the sequences SEQ ID NO: 2 or SEQ ID NO: 4 for the production of unsaturated fatty acids.

The invention is illustrated in greater detail by the examples which follow:

EXAMPLES

Example 1

General Cloning Methods

The cloning methods, such as by way of example restriction cleavages, agarose gel electrophoresis, purification of DNA fragments, transfer of nucleic acids to nitrocellulose and nylon membranes, linkage of DNA fragments, transformation of *Escherichia coli* cells, culture of bacteria and sequence analysis of recombinant DNA, were carried out as described in Sambrook et al. (1989) (Cold Spring Harbor Laboratory Press: ISBN 0-87969-309-6).

Example 2

Sequence Analysis of Recombinant DNA

Sequencing of recombinant DNA molecules was done using a laser fluorescence DNA sequencer from ABI, by the method of Sanger (Sanger et al. (1977) Proc. Natl. Acad. Sci. USA 74, 5463-5467). Fragments resulting from a polymerase chain reaction were sequenced and checked to prevent polymerase errors in the constructs to be expressed.

Example 3

Cloning of PUFA-Specific Desaturases from *Primula cortusoides* and *Primula lutoides*

While the majority of the higher plants (Angiospermae, Gymnospermae) do not synthesize Δ6-desaturated fatty acids, the precursors for the synthesis of PUFA, the families Boraginaceae, Saxifragaceae and Primulaceae comprise species which accumulate this fatty acid. This is why members of these species are raw material for identifying Δ6-desaturases.

*Primula cortusoides* and *Primula lutoides* (Eukaryota; Plantae, Tracheophyta, Angiospermae, Primulales, Primulaceae) were selected since in species Δ6-desaturated products, and here mainly 18:4$^{Δ6,9,12,15}$, the precursor of EPA, accumulate in the seed. To isolate DNA, seeds were obtained from Chiltern Seeds, Cumbria, UK, and grown under the following conditions.

Prior to sowing, the seeds were soaked for at least 3 hours in cold water. The seeds were sown on potting compost with 20% sand, spaced at at least 1 cm. Under the compost there is a layer of Perlite (⅓ volume relative to the compost). After sowing, the seeds were covered with Perlite, watered generously from above and kept under long-day conditions (16 hours light, 100 μEm-2s-1, 21° C., 8 hours night, 17° C.).

Total RNA was extracted as described in Sayanova et al. 1997, Proc. Natl. Acad. Sci. USA 94, 4211-4216. First-strand cDNA was synthesized starting from total RNA by means of the SMART RACE cDNA Amplification Kit (Clontech) following the manufacturer's instructions.

To identify novel desaturase genes, the following degenerate primers were employed for the amplification:

(SEQ ID NO: 13)
Deg1:
5'-GGITCA(C/T)GA(T/C)(T/G/A)(C/G)IGGICA(C/T)TA-3'

(SEQ ID NO: 14)
Deg2:
5'-CC(A/G)TCIGT(A/G)T(T/G)IA(G/A)IGC(T/C)TCCCA-3'

The following conditions were used for the amplification:
2 minutes at 95° C., followed by 30 cycles of 30 seconds at 94° C., 30 seconds at 55-72° C., 2 minutes at 72° C. Finally, elongation was performed for 10 minutes at 72° C. PCR amplicons were cloned into pGEM-T (Promega) following the manufacturer's instructions and sequenced. The sequence data obtained were employed for preparing full-length clones. To this end, primers which were gene-specific at the 5° and 3° ends were synthesized and amplified starting from the cDNA.

In each case one sequence with similarity to desaturase genes was identified.

| Gene | Species | Nucleotide | SEQ ID NO: |
|---|---|---|---|
| Cort6 | *P. cortusoides* | 1353 bp | 3 |
| Lut6 | *P. lutoides* | 1350 bp | 1 |

Example 4

Cloning of Expression Plasmids for the Heterologous Expression of *P. cortusoides* and *P. lutoides* Genes in Yeasts For the heterologous expression in yeasts, the corresponding sequences were amplified via PCR, using suitable specific primers, and cloned into the yeast expression vector pYES2 (Invitrogen) via KpnI-SacI. In doing so, exclusively the open reading frames of the genes which coded for the PUFA proteins were amplified. In addition, a restriction sequence for KpnI and a Kozak sequence (Cell 1986, 44:283-292) was attached at the 5' end and a restriction sequence for SacI was attached at the 3' end.

| Gene | Base pairs | Primer | SEQ ID NO: |
|---|---|---|---|
| Cort6 | 1353 | Fwd:<br>GGTACCATGGCCAACCCATCAAAAAAC | 5 |
| | | Rvs:<br>3' CCTTCCACACACACGGATAAGAGCTCC | 6 |
| Lut6 | 1350 | Fwd:<br>GGTACCATGGCTAACAAATCTCAAAC | 7 |
| | | Rvs:<br>3' CTGTTCAAACTCTCGGGTGAGGAGCT | 8 |

Composition of the PCR mix (50 μl):
5.00 μl template cDNA
5.00 μl 10× buffer (Advantage polymerase)+25 mM MgCl$_2$
5.00 μl 2 mM dNTP
1.25 μl of each primer (10 pmol/μl of the 5'-ATG and of the 3'-Stopp primer)
0.50 μl Advantage polymerase
Clontech's Advantage polymerase is employed.

PCR reaction conditions:
Annealing temperature: 1 minute at 55° C.
Denaturation temperature: 1 minute at 94° C.
Elongation temperature: 2 minutes at 72° C.
Number of cycles: 35

The PCR products and the vector pYES2 were incubated for one hour at 37° C. with the restriction enzymes KpnI and SacI, and the ligation reaction was carried out by means of the Rapid Ligation Kit (Roche) following the manufacturer's instructions. The incubation reactions were then transformed into E. coli DH5α cells (Invitrogen) following the manufacturer's instructions. Positive clones were identified by PCR (see reaction above), and the plasmid DNA was isolated (Qiagen Dneasy). The resulting plasmids pYCort6 and pYLut6 were verified by sequencing and transformed into the Saccharomyces strain W303-1A by means of the lithium acetate method. pYES2 (blank vector) was transformed in parallel for control purposes. The transformed yeasts were selected on complete minimal medium (CMdum) agar plates supplemented with 2% glucose, but without uracil.

For the expression of the P. cortusoides and P. lutoides genes, precultures of in each case 5 ml CMdum liquid medium supplemented with 2% (w/v) raffinose, but without uracil, were first inoculated with in each case one selected transformant and incubated for 2 days at 30° C., 200 rpm.

Then, 5 ml of CMdum liquid medium (without uracil) supplemented with 2% raffinose and 300 µM of the various fatty acids were inoculated with the precultures to an $OD_{600}$ of 0.05. Expression was induced by the addition of 2% (w/v) galactose. The cultures are incubated at 22° C. for a further 96 hours.

Example 5

Cloning of Expression Plasmids for Expression in Plants

For the transformation of plants, further transformation vectors based on pBIN19-35S (Bevan M. (1984) Binary Agrobacterium vectors for plant transformation. Nucl. Acids Res. 18:203) were generated. To this end, BamHI-XbaI cleavage sites were introduced at the 5' and the 3' end of the coding sequence, using the following primer pairs:

| Gene | Base pairs | Primer | SEQ ID NO |
|---|---|---|---|
| Cort6 | 1353 bp | Fwd: GGATCCACCATGGCCAACCCATCAAAAAAC | 9 |
| | | Rvs: 3' CCTTCCACACACACGGATAAGGTCTAGA | 10 |
| Lut6 | 1350 bp | Fwd: GGATCCACCATGGCTAACAAATCTCAAAC | 11 |
| | | Rvs: 3' CTGTTCAAACTCTCGGGTGAGGTCTAGA | 12 |

Composition of the PCR mix (50 µl):
5.00 µl template cDNA
5.00 µl 10× buffer (Advantage polymerase)+25 mM $MgCl_2$
5.00 µl 2 mM dNTP
1.25 µl of each primer (10 pmol/µl)
0.50 µl Advantage polymerase
Clontech's Advantage polymerase is employed.

The PCR products and the vector pBin19-35S were incubated for one hour at 37° C. with the restriction enzymes BamHI and XbaI, and the ligation reaction was carried out by means of the Rapid Ligation Kit (Roche) following the manufacturer's instructions. The incubation reactions were then transformed into E. coli DH5α cells (Invitrogen) following the manufacturer's instructions. Positive clones were identified by PCR (see reaction above), and the plasmid DNA was isolated (Qiagen Dneasy). The resulting plasmids pBIN-Cort6 and pBIN-Lut6 were then transformed into Agrobacterium tumefaciens GC3101 by electroporation and plated onto agar plates with 2% YEB medium+kanamycin. Kanamycin-tolerant cells were selected and employed for the transformation of Arabidopsis thaliana.

Example 6

Expression of P. cortusoides and P. lutoides Genes in Yeasts

Yeasts which had been transformed with the plasmid pYES2 or the plasmids pYES-Cort6 and pYES-Lut6 as per example 4 were analyzed as follows: The yeasts as from the main cultures were harvested by centrifugation (100×g, 5 min, 20° C.) and washed with 100 mM $NaHCO_3$, pH 8.0 in order to remove residual medium and fatty acids. Fatty acid methyl esters (FAMEs) were prepared from the yeast cell sediments by acid methanolysis. To this end, the cell sediments were incubated for 1 hour at 80° C. with 2 ml of 1 N methanolic sulfuric acid and 2% (v/v) dimethoxypropane. The FAMEs were extracted by two extractions with petroleum ether (PE). To remove non-derivatized fatty acids, the organic phases were washed in each case once with 2 ml of 100 mM $NaHCO_3$, pH 8.0, and 2 ml of distilled water. Thereafter, the PE phases were dried with $Na_2SO_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis were as follows: the oven temperature was programmed from 50° C. to 250° C. with a rate of 5° C./min and finally for 10 minutes at 250° C. (holding).

The signals were identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 7

Functional Characterization

The activity and substrate specificity of the individual genes were determined by expression and feeding of various fatty acids. The substrate specificity of desaturases can be determined after expression in yeasts by feeding by means of various fatty acids. Descriptions for the determination of the individual activities can be found in WO 93/11245, WO 94/11516, WO 93/06712, U.S. Pat. No. 5,614,393, U.S. Pat. No. 5,614,393, WO 96/21022, WO0021557 and WO 99/27111, Qiu et al. 2001, J. Biol. Chem. 276, 31561-31566 for Δ4-desaturases, Hong et al. 2002, Lipids 37,863-868 for Δ5-desaturases.

a) Characterization of Cort6:

The construct pYES-Cort6 was tested in yeast by feeding various fatty acids. Surprisingly, it was possible to demonstrate in this experiment that new fatty acids have been formed after feeding with the fatty acids $18:2^{\Delta 9, 12}$ and $18:3^{\Delta 9, 12, 15}$ (FIG. 1).

FIG. 1: Gas-chromatographic analysis of yeasts which comprise the plasmid pYCort6 and which have been fed 18:2. The newly formed fatty acid is $\gamma 18:3^{\Delta 6, 9, 12}$ ($\gamma$-linolenic acid=GLA).

As the result of the newly formed fatty acid, a $\Delta 6$-desaturase activity was detected for Cort6. Here, the enzyme was capable of utilizing 18:2 and 18:3 as its substrate.

b) Characterization of Lut6:

Surprisingly, it was demonstrated, after feeding of 18:3, that Lut6 has a $\Delta 6$-desaturase activity (FIG. 2).

FIG. 2: Fatty acid pattern of yeasts had been transformed with the construct pYLut6 and fed the fatty acid $18:3^{\Delta 9, 12, 15}$. The corresponding fatty acids are identified. SDA (stearidonic acid) corresponds to $18:4^{\Delta 6, 9, 12, 15}$.

Thus, the activity of Lut6 corresponds to the activity of a $\Delta 6$-desaturase.

Example 8

Generation of Transgenic Plants a) Generation of Transgenic Oilseed Rape Plants (Modified in Accordance with Moloney et al., 1992, Plant Cell Reports, 8:238-242)

To generate transgenic oilseed rape plants, binary vectors like the pBIN-35S plasmids generated in example 5 were transformed into *Agrobacterium tumefaciens* GC3101 (Deblaere et al, 1984, Nucl. Acids. Res. 13, 4777-4788). To transform oilseed rape plants (cv. Drakkar, NPZ Nordeutsche Pflanzenzucht, Hohenlieth, Germany), a 1:50 dilution of an overnight culture of a positively transformed agrobacterial colony in Murashige-Skoog medium (Murashige and Skoog 1962 Physiol. Plant. 15, 473) supplemented with 3% sucrose (3MS medium) was used. Petioles or hypocotyledons of freshly germinated sterile rape plants (each approx. 1 cm²) were incubated in a Petri dish with a 1:50 agrobacterial dilution for 5-10 minutes. This was followed by 3-day co-incubation in the dark at 25° C. on 3MS medium supplemented with 0.8% Bacto agar. After 3 days, culturing was continued with 16 hours light/8 hours/darkness and in a weekly cycle on MS medium supplemented with 500 mg/l Claforan (sodium cefotaxime), 50 mg/l kanamycin, 20 microM benzylaminopurine (BAP) and 1.6 g/l glucose. Growing shoots were transferred onto MS medium supplemented with 2% sucrose, 250 mg/l Claforan and 0.8% Bacto agar. If no roots had formed after 3 weeks, 2-indolebutyric acid was added to the medium as growth hormone to promote rooting.

Regenerated shoots were obtained on 2MS medium supplemented with kanamycin and Claforan, transferred into soil after rooting and, after culturing, grown for 2 weeks in a controlled-environment chamber, brought to flower, mature seeds were harvested and studied for expression of the desaturase or elongase genes by means of lipid analyses as described by way of example in Qiu et al. 2001, J. Biol. Chem. 276, 31561-31566.

b) Generation of Transgenic Linseed Plants

Transgenic linseed plants may be generated, for example, by the method of Bell et al., 1999, In Vitro Cell. Dev. Biol.-Plant. 35(6):456-465 by means of particle bombardment.

Agrobacteria-mediated transformations can be generated for example as described by Mlynarova et al. (1994), Plant Cell Report 13: 282-285.

Example 9

Lipid Extraction from Leaves

The effect of genetic modification in plants, fungi, algae, ciliates or on the production of a desired compound (such as a fatty acid) can be determined by growing the modified microorganisms or the modified plant under suitable conditions (such as those described hereinbelow) and analyzing the medium and/or the cellular components for the increased production of the desired product (i.e. of lipids or of a fatty acid). These analytical techniques are known to the skilled worker and comprise spectroscopy, thin-layer chromatography, various types of staining methods, enzymatic and microbiological methods and analytical chromatography, such as high-performance liquid chromatography (see, for example, Ullman, Encyclopedia of Industrial Chemistry, Vol. A2, pp. 89-90 and pp. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", pp. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, pp. 1-27, VCH: Weinheim; and Dechow, F. J. (1989) Separation and purification techniques in biotechnology, Noyes Publications).

In addition to the abovementioned methods, plant lipids are extracted from plant material as described by Cahoon et al. (1999) Proc. Natl. Acad. Sci. USA 96 (22):12935-12940, and Browse et al. (1986) Analytic Biochemistry 152:141-145. The qualitative and quantitative analysis of lipids or fatty acids is described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research, Oxford: Pergamon Press, 1 (1952)-16 (1977) under the title: Progress in the Chemistry of Fats and Other Lipids CODEN.

One example is the analysis of fatty acids (abbreviations: FAME: fatty acid methyl ester; GC-MS, gas-liquid chromatography/mass spectrometry; TAG, triacylglycerol; TLC, thin-layer chromatography).

The unambiguous detection for the presence of fatty acid products can be obtained by analyzing recombinant organisms using analytical standard methods: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometric methods], Lipide 33:343-353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 microm, 0.32 mm) at a temperature gradient of between 170° C. and 240° C. for 20 minutes and 5 minutes at 240° C. The identity of the resulting fatty acid methyl esters must be defined using standards which are available from commercial sources (i.e. Sigma).

Plant material is initially homogenized mechanically by comminuting with a pestle and mortar to make it more amenable to extraction. This is followed by heating at 100° C. for 10 minutes and, after cooling on ice, by resedimentation. The cell sediment is hydrolyzed for one hour at 90° C. with 1 M methanolic sulfuric acid and 2% dimethoxypropane, and the lipids are transmethylated. The resulting fatty acid methyl esters (FAMEs) are extracted in petroleum ether. The extracted FAMEs are analyzed by gas liquid chromatography using a capillary column (Chrompack, WCOT Fused Silica, CP-Wax-52 CB, 25 m, 0.32 mm) and a temperature gradient of from 170° C. to 240° C. in 20 minutes and 5 minutes at 240° C. The identity of the fatty acid methyl esters is confirmed by comparison with corresponding FAME standards (Sigma). The identity and position of the double bond can be analyzed further by suitable chemical derivatization of the FAME mixtures, for example to give 4,4-dimethoxyoxazoline derivatives (Christie, 1998) by means of GC-MS.

Analysis of transgenic *Arabidopsis* plants which express Cort6:

Plants which had been transformed as in example 5 with the plasmids pBIN-Cort6 and pBIN-Lut6 were analyzed for modified fatty acids. The initial material employed was leaves which were extracted and analyzed by gas chromatography as described hereinabove.

The generation of novel fatty acids was demonstrated for both plasmids (FIGS. 3 and 4). In this context, it was demonstrated that the enzyme Cort6 preferentially converts the fatty acid $18:2^{\Delta 9,12}$, which is endogenally present, while Lut6, surprisingly, preferentially converts $18:3^{\Delta 9,12,15}$ into SDA ($18:4^{\Delta 6,9,12,15}$). From this it can be concluded that the two enzymes can be employed in a plant background preferentially for the production of GLA or SDA, precursors of the PUFA ARA and EPA, respectively.

FIG. 3: Gas-chromatographic analysis of the fatty acids from leaf material of *Arabidopsis* plants which had been transformed with the plasmid pBiN-Cort6.

---

We claim:

1. A method of producing γ-linolenic acid ($18:3^{\Delta 6,9,12}$) or stearidonic acid ($18:4^{\Delta 6,9,12,15}$) or a method of producing γ-linolenic acid ($18:3^{\Delta 6,9,12}$) and stearidonic acid ($18:4^{\Delta 6,9,12,15}$) in a transgenic plant, wherein the transgenic plant comprises at least 10% by weight of oleic acid based on the total fatty acid content and wherein the method comprises:
   a) introducing, into a plant, a nucleic acid sequence which codes for a Δ6-desaturase,
   b) expressing, in the plant, the nucleic acid sequence which codes for a Δ6-desaturase, and
   c) growing and harvesting the plant,
   wherein the nucleic acid sequence which codes for a Δ6-desaturase comprises:
   i) the nucleic acid sequence of SEQ ID NO: 1,
   ii) a nucleic acid sequence which, as the result of the degeneracy of the genetic code, can be derived from the amino acid sequence of SEQ ID NO: 2, or
   iii) a nucleic acid sequence which codes for a polypeptide having at least 95% homology with the amino acid sequence of SEQ ID NO: 2 and having Δ6-desaturase activity,
   wherein the Δ6-desaturase encoded by said nucleic acid sequence has a substrate specificity for α-linolenic acid which is more than 20 times higher than the substrate specificity for linoleic acid,
   and wherein the plant is selected from the group consisting of plants of the family Brassicaceae or Linaceae, soya, oilseed rape, and sunflower.

2. The method of claim 1, wherein the nucleic acid sequence is linked operably with a promoter, a terminator, or a promoter and a terminator.

3. The method of claim 1, wherein the activity of the Δ6-desaturase encoded by said nucleic acid sequence leads to an increased Δ6-$C_{18}$-fatty acid content in the plant.

4. The method of claim 1, wherein the Δ6-desaturase encoded by said nucleic acid sequence accepts only α-linolenic acid as its substrate and linoleic acid is not converted.

5. The method of claim 1, wherein unsaturated fatty acids γ-linolenic acid ($18:3^{\Delta 6,9,12}$), stearidonic acid ($18:4^{\Delta 6,9,12,15}$), or γ-linolenic acid ($18:3^{\Delta 6,9,12}$) and stearidonic acid ($18:4^{\Delta 6,9,12,15}$) are increased in the seeds of the plant.

6. The method of claim 5, wherein the seeds are isolated from the plant.

7. The method of claim 1, wherein the unsaturated fatty acids γ-linolenic acid ($18:3^{\Delta 6,9,12,15}$), stearidonic acid ($18:4^{\Delta 6,9,12,15}$), γ-linolenic acid ($18:3^{\Delta 6,9,12}$) and stearidonic acid ($18:4^{\Delta 6,9,12,15}$) are isolated in the form of an oil, lipid or in the form of the free fatty acids from the plant or their seeds.

8. The method of claim 7, wherein the unsaturated fatty acids present in the oil or in the lipids are isolated in the form of the free fatty acids.

9. The method of claim 7, wherein the oils, lipids or free fatty acids are mixed with other animal, microbial or plant oils, lipids or fatty acids to give fatty acid compositions.

10. The method of claim 7, wherein the oils, lipids, free fatty acids, or fatty acid compositions containing the same, are added to foods, feeds, cosmetics or pharmaceuticals.

11. An isolated nucleic acid encoding a polypeptide with Δ6-desaturase activity, which preferentially utilizes α-linolenic acid as substrate over linoleic acid, comprising a nucleic acid sequence selected from the group consisting of:
   a) the nucleic acid sequence of SEQ ID NO: 1,
   b) a nucleic acid sequence which, as the result of the degeneracy of the genetic code, can be derived from the amino acid sequence of SEQ ID NO: 2, and
   c) a nucleic acid sequence which codes for a polypeptide having at least 95% homology with the amino acid sequence of SEQ ID NO: 2 and having Δ6-desaturase activity.

12. The isolated nucleic acid of claim 11, wherein the isolated nucleic acid is derived from a plant.

13. The isolated nucleic acid of claim 11, wherein the isolated nucleic acid is derived from the family Primulaceae.

14. A gene construct comprising the isolated nucleic acid of claim 11, wherein the isolated nucleic acid is linked operably with one or more regulatory signals.

15. The gene construct of claim 14, wherein the gene construct comprises a biosynthetic gene of the fatty acid or lipid metabolism selected from the group consisting of acyl-CoA dehydrogenase(s), acyl-ACP[=acyl carrier protein] desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases and fatty acid elongase(s).

16. The gene construct of claim 14, wherein the gene construct additionally comprises a biosynthetic gene of the fatty acid or lipid metabolism selected from the group consisting of Δ4-desaturases, Δ5-desaturases, Δ8-desaturases, Δ9-desaturases, Δ12-desaturases, Δ5-elongases, Δ6-elongases and Δ9-elongases.

17. A vector comprising the isolated nucleic acid of claim 11 or a gene construct comprising said isolated nucleic acid.

18. A transgenic plant of the family Brassicaceae or Linaceae, comprising the isolated nucleic acid of claim 11, a gene construct comprising said isolated nucleic acid, or a vector comprising the said isolated nucleic acid or said gene construct.

* * * * *